United States Patent [19]

Rose et al.

[11] Patent Number: 5,373,858
[45] Date of Patent: Dec. 20, 1994

[54] APPARATUS AND METHOD FOR DETERMINING ANGLE OF INCLINATION AND RANGE OF MOTION OF VARIOUS HUMAN JOINTS THEREFROM

[75] Inventors: Robert W. Rose; John D. Truelove, both of Evansville; Carl K. Barniak, Newburgh, all of Ind.

[73] Assignee: Technostix, Inc., Evansville, Ind.

[21] Appl. No.: 89,787

[22] Filed: Jul. 9, 1993

[51] Int. Cl.$^5$ .............................................. A61B 5/00
[52] U.S. Cl. .................................................. 128/782
[58] Field of Search ....................... 128/774, 781, 782; 33/512, 355 R

[56] References Cited

U.S. PATENT DOCUMENTS

| | | | |
|---|---|---|---|
| 4,571,834 | 2/1986 | Fraser et al. | 128/782 |
| 4,800,897 | 1/1989 | Nilsson | 128/782 |
| 4,928,709 | 5/1990 | Allison et al. | 128/782 |
| 5,042,505 | 8/1991 | Mayer et al. | 128/782 |
| 5,203,346 | 4/1993 | Fuhr et al. | 128/782 |
| 5,228,454 | 7/1993 | Siegler | 128/782 |

*Primary Examiner*—Max Hindenburg
*Attorney, Agent, or Firm*—Middleton & Reutlinger

[57] ABSTRACT

An apparatus and method used to determine angle of inclination and the range of motion of various human joints therefrom, such as, for example, cervical flexion. The apparatus of one preferred embodiment is a computerized arthrometer which is a stand-alone automated apparatus. Output can be provided to a printer for hard copy or to a computer for storage or further manipulation of data. Each sensor or inclinometer used in the preferred embodiment employs a pair of Hall effect transducers spaced about a rotating ring magnet. The voltage output of the transducers can be evaluated to accurately determine the angle of inclination. In another preferred embodiment, instead of the magnet and transducers, the sensors can include circular sensor having six capacitive sectors, each sector changing capacitance as the circular sensor is rotated. The six capacitance values are evaluated to determine the angle of inclination. Another embodiment incorporates the apparatus into readily available "personal computers" ("PCs"). By employing a pair of sensors for selected range of motion tests, measurement accuracy is increased by compensating for the effects of secondary motion, for example, compensating for forward or backward movement of the torso when measuring cervical flexion or cervical extension, respectively.

17 Claims, 20 Drawing Sheets

FIGURE NO. 7

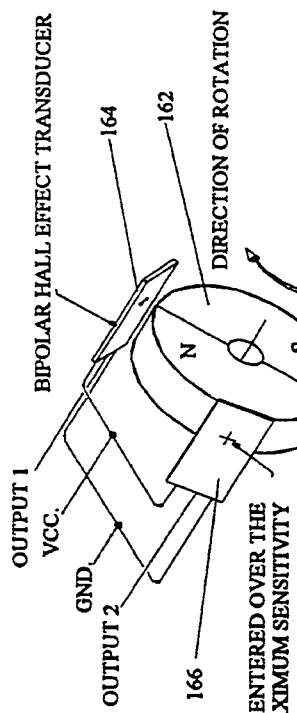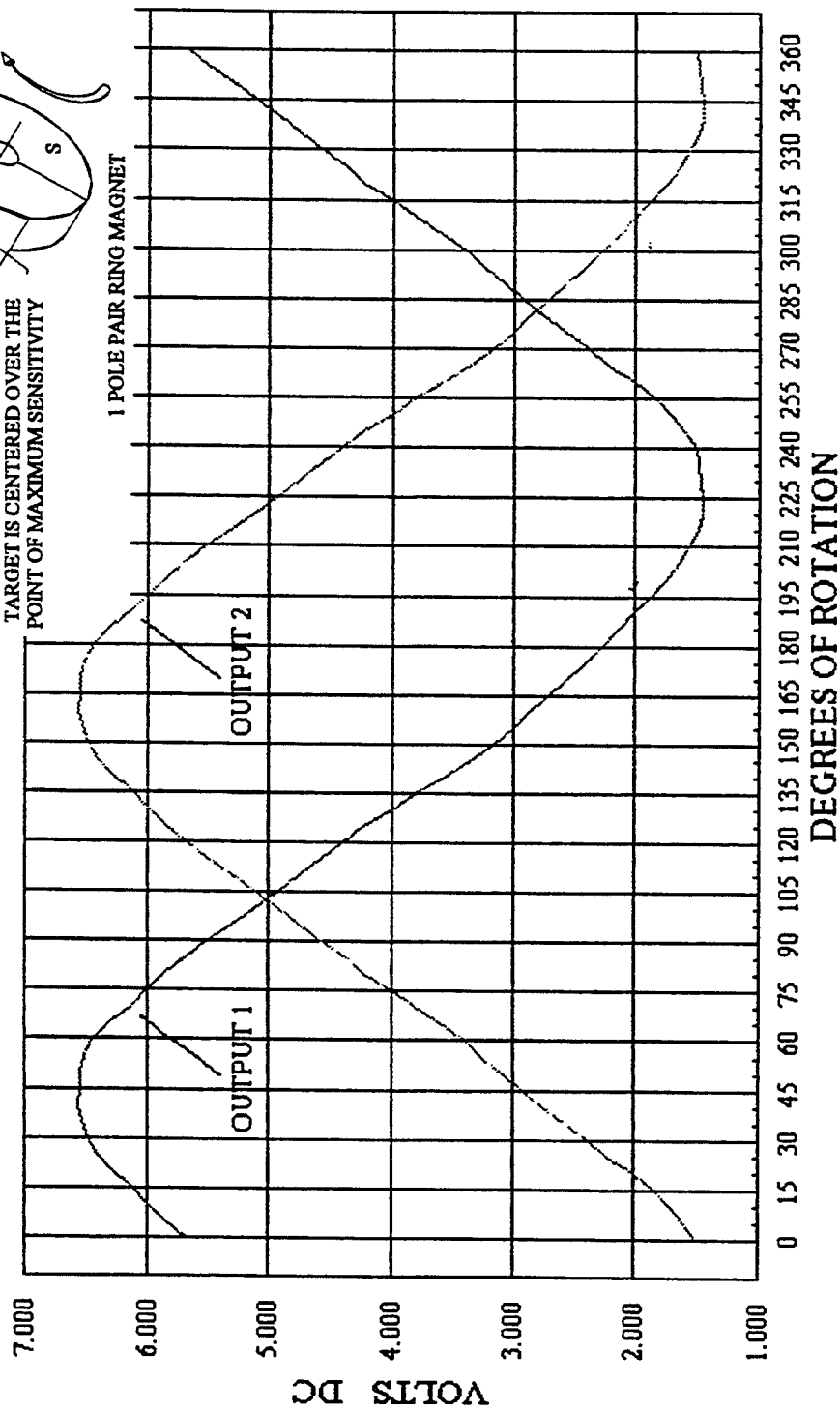
Fig. 8
RESPONSE OF ROTATING MAGNET

HALL EFFECT SENSOR
LOOKUP TABLE FOR DEGREES

| DEGREES | Sensor 1 Voltage | Sensor 2 Voltage |
|---|---|---|
| 45 | 6.550 | 2.925 |
| 46 | 6.548 | 2.956 |
| 47 | 6.546 | 2.987 |
| 48 | 6.544 | 3.018 |
| 49 | 6.542 | 3.049 |
| 50 | 6.540 | 3.080 |
| 51 | 6.535 | 3.114 |
| 52 | 6.530 | 3.148 |
| 53 | 6.525 | 3.182 |
| 54 | 6.520 | 3.216 |
| 55 | 6.515 | 3.250 |
| 56 | 6.499 | 3.280 |
| 57 | 6.483 | 3.310 |
| 58 | 6.467 | 3.340 |
| 59 | 6.451 | 3.370 |
| 60 | 6.435 | 3.400 |
| 61 | 6.405 | 3.440 |
| 62 | 6.375 | 3.480 |
| 63 | 6.345 | 3.520 |
| 64 | 6.315 | 3.560 |
| 65 | 6.285 | 3.600 |

| DEGREES | Sensor 1 Voltage | Sensor 2 Voltage |
|---|---|---|
| 65 | 6.285 | 3.600 |
| 66 | 6.253 | 3.640 |
| 67 | 6.221 | 3.680 |
| 68 | 6.189 | 3.720 |
| 69 | 6.157 | 3.760 |
| 70 | 6.125 | 3.800 |
| 71 | 6.100 | 3.840 |
| 72 | 6.075 | 3.880 |
| 73 | 6.050 | 3.920 |
| 74 | 6.025 | 3.960 |
| 75 | 6.000 | 4.000 |
| 76 | 5.970 | 4.045 |
| 77 | 5.940 | 4.090 |
| 78 | 5.910 | 4.135 |
| 79 | 5.880 | 4.180 |
| 80 | 5.850 | 4.225 |
| 81 | 5.815 | 4.255 |
| 82 | 5.780 | 4.285 |
| 83 | 5.745 | 4.315 |
| 84 | 5.710 | 4.345 |
| 85 | 5.675 | 4.375 |
| 86 | 5.640 | 4.415 |
| 87 | 5.605 | 4.455 |
| 88 | 5.570 | 4.495 |
| 89 | 5.535 | 4.535 |
| 90 | 5.500 | 4.575 |

Fig. 9

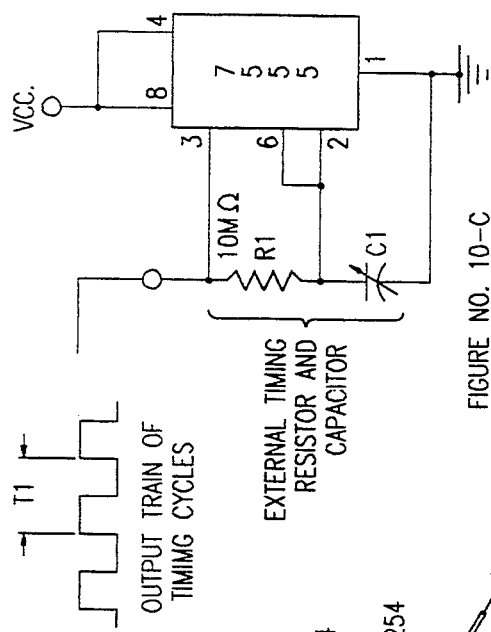
FIGURE NO. 10-C
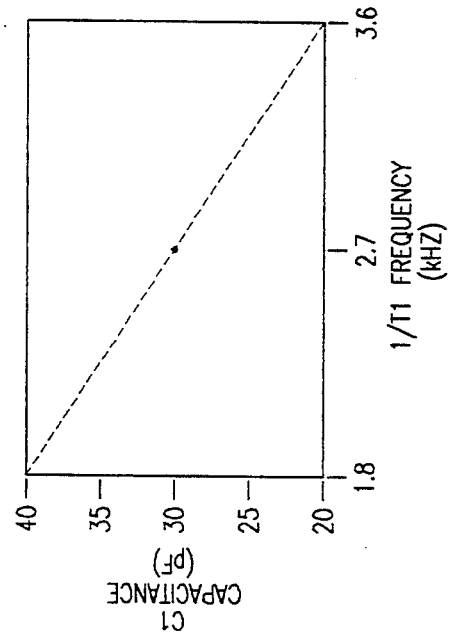
FIGURE NO. 10-D
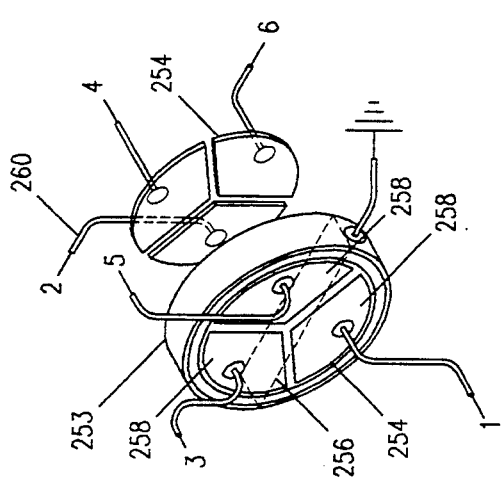
FIGURE NO. 10-B
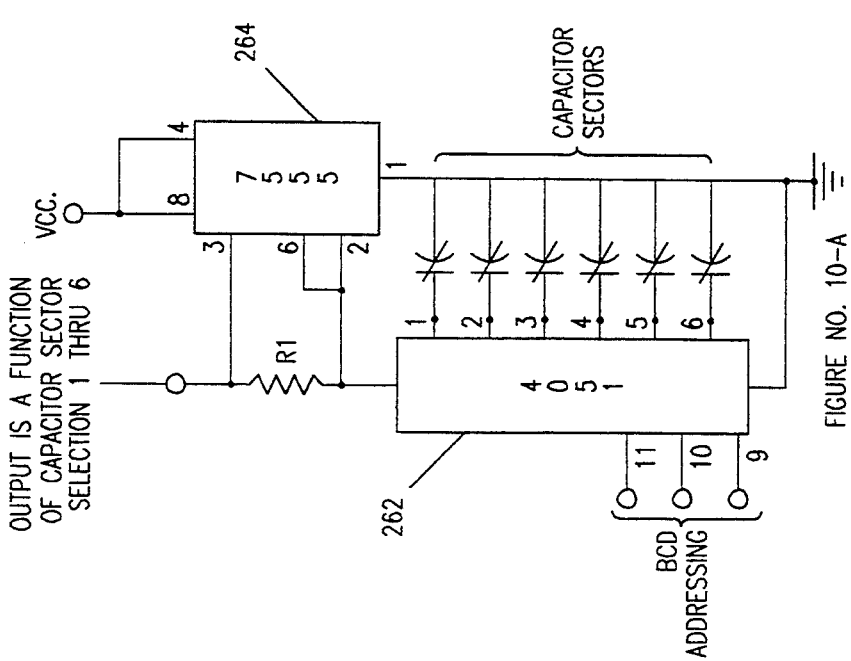
FIGURE NO. 10-A Capacitive Sensor Lookup Table
Time Value For 35 Clock Pulses (in milliseconds)

| Degree | Sector 1 | Sector 2 | Sector 3 | Sector 4 | Sector 5 | Sector 6 | Ratio |
|---|---|---|---|---|---|---|---|
| 358 | 48.529 | 34.084 | 26.801 | 26.500 | 36.430 | 50.425 | 1.47943 |
| 359 | 48.761 | 34.297 | 26.810 | 26.493 | 36.204 | 50.219 | 1.46424 |
| 0 | 48.930 | 34.494 | 26.814 | 26.482 | 35.953 | 49.996 | 1.44941 |
| 1 | 49.156 | 34.705 | 26.834 | 26.469 | 35.742 | 49.796 | 1.43484 |
| 2 | 49.366 | 34.928 | 26.847 | 26.443 | 35.527 | 49.570 | 1.41921 |
| 3 | 49.586 | 35.132 | 26.858 | 26.434 | 35.302 | 49.349 | 1.40467 |
| 4 | 49.789 | 35.341 | 26.888 | 26.430 | 35.098 | 49.119 | 1.38986 |
| 5 | 50.004 | 35.560 | 26.908 | 26.421 | 34.874 | 48.906 | 1.37531 |
| 6 | 50.219 | 35.775 | 26.925 | 26.411 | 34.670 | 48.681 | 1.36075 |
| 7 | 50.414 | 35.992 | 26.947 | 26.393 | 34.455 | 48.448 | 1.34608 |
| 8 | 50.610 | 36.222 | 26.964 | 26.376 | 34.230 | 48.231 | 1.33154 |
| 9 | 50.820 | 36.428 | 27.010 | 26.363 | 34.028 | 48.008 | 1.31789 |
| 10 | 50.998 | 36.645 | 27.036 | 26.363 | 33.815 | 47.799 | 1.30438 |
| 11 | 51.191 | 36.873 | 27.077 | 26.359 | 33.602 | 47.569 | 1.29008 |
| 12 | 51.361 | 37.081 | 27.135 | 26.348 | 33.396 | 47.339 | 1.27664 |
| 13 | 51.510 | 37.305 | 27.196 | 26.332 | 33.190 | 47.116 | 1.26299 |
| 14 | 51.656 | 37.524 | 27.263 | 26.339 | 32.982 | 46.884 | 1.24944 |
| 15 | 51.803 | 37.750 | 27.348 | 26.335 | 32.767 | 46.660 | 1.23603 |
| 16 | 51.921 | 37.973 | 27.435 | 26.326 | 32.572 | 46.450 | 1.22324 |
| 17 | 52.036 | 38.186 | 27.541 | 26.317 | 32.363 | 46.215 | 1.21026 |
| 18 | 52.129 | 38.418 | 27.658 | 26.306 | 32.151 | 45.985 | 1.19696 |
| 19 | 52.216 | 38.633 | 27.784 | 26.302 | 31.966 | 45.760 | 1.18448 |
| 20 | 52.292 | 38.861 | 27.925 | 26.296 | 31.760 | 45.532 | 1.17166 |
| 21 | 52.346 | 39.080 | 28.064 | 26.304 | 31.552 | 45.293 | 1.15898 |
| 22 | 52.415 | 39.310 | 28.214 | 26.296 | 31.350 | 45.074 | 1.14663 |
| 23 | 52.476 | 39.536 | 28.368 | 26.291 | 31.146 | 44.846 | 1.13431 |
| 24 | 52.511 | 39.755 | 28.540 | 26.285 | 30.953 | 44.612 | 1.12217 |
| 25 | 52.548 | 39.976 | 28.711 | 26.280 | 30.760 | 44.371 | 1.10994 |
| 26 | 52.572 | 40.197 | 28.882 | 26.285 | 30.573 | 44.156 | 1.09849 |
| 27 | 52.600 | 40.425 | 29.056 | 26.283 | 30.384 | 43.924 | 1.08656 |
| 28 | 52.632 | 40.638 | 29.219 | 26.276 | 30.189 | 43.700 | 1.07535 |
| 29 | 52.641 | 40.868 | 29.431 | 26.285 | 29.993 | 43.457 | 1.06335 |
| 30 | 52.663 | 41.089 | 29.603 | 26.270 | 29.805 | 43.238 | 1.05230 |
| 31 | 52.671 | 41.328 | 29.807 | 26.276 | 29.622 | 43.003 | 1.04053 |

Fig. 13

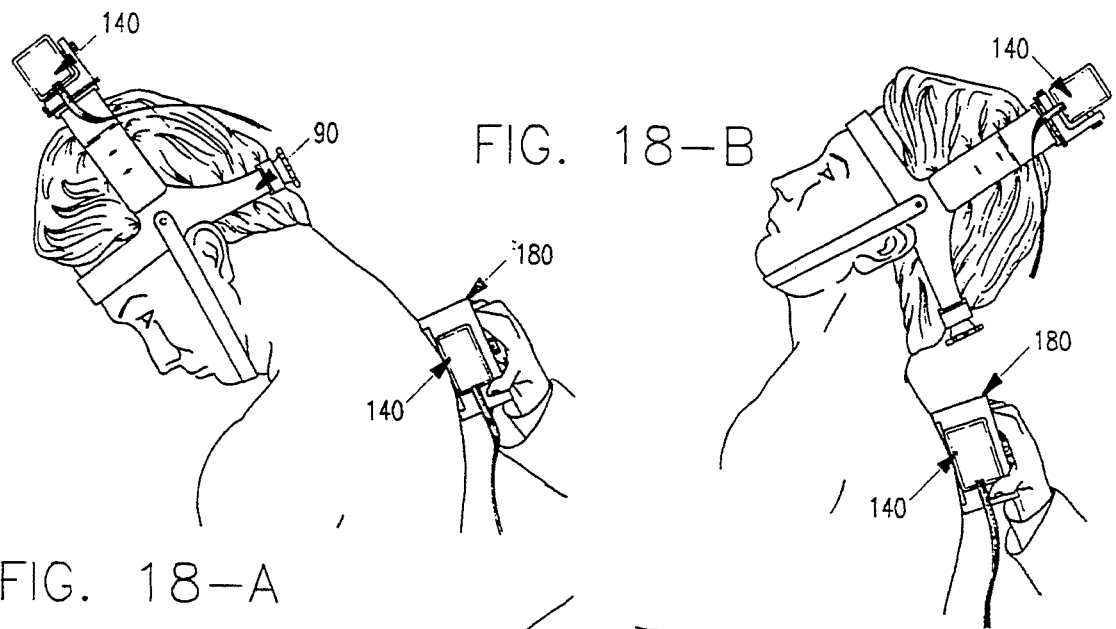
FIG. 18-B
FIG. 18-A
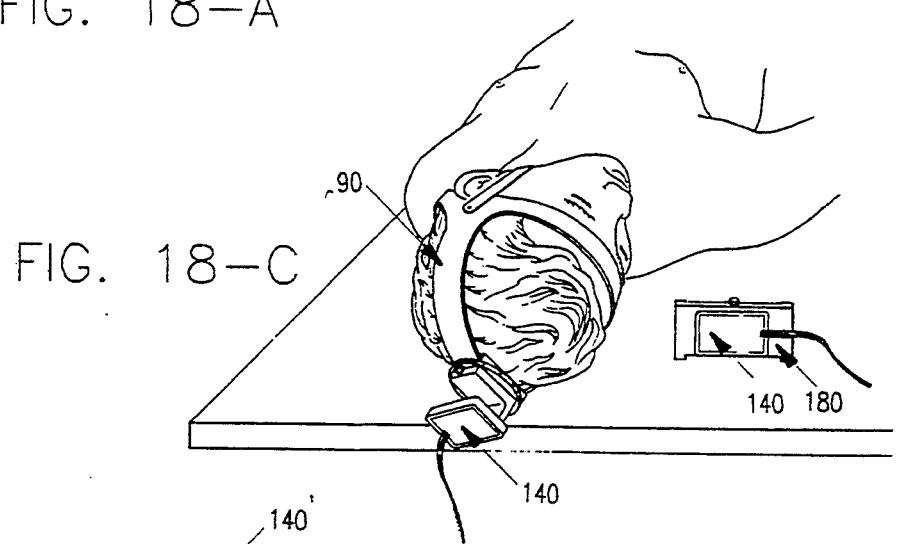
FIG. 18-C
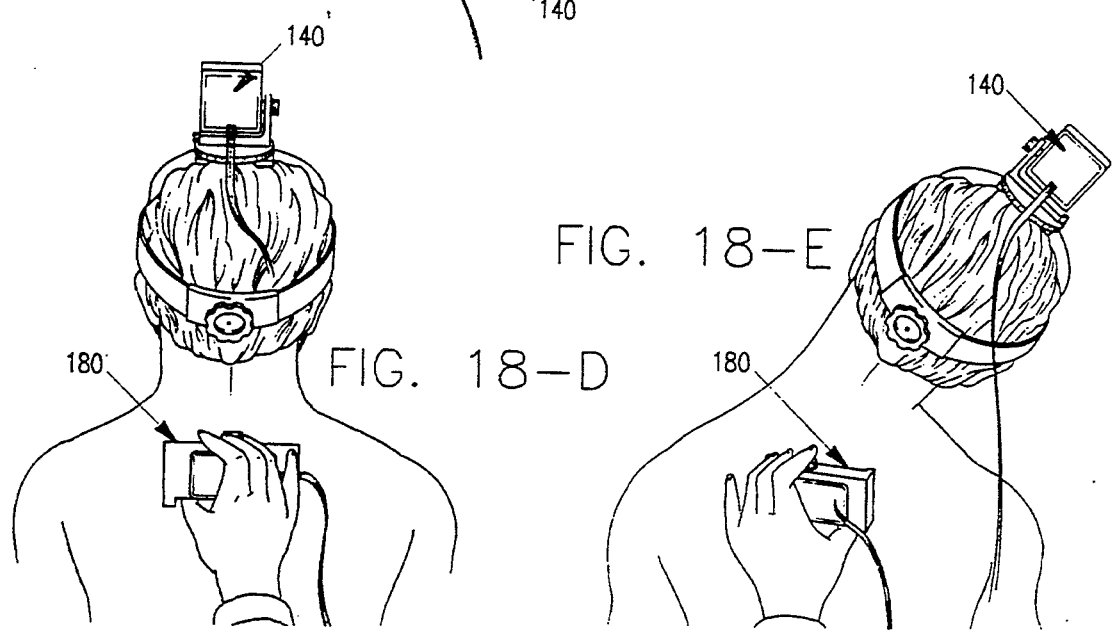
FIG. 18-E
FIG. 18-D

FIG. 19

PATIENT:       BILL SMITH           TESTING DATE:   09/15/92
FILE NUMBER:   2007                 PHYSICIAN:      R.R.
AGE:           30                   TECHNICIAN:     J.G.

THIS PATIENT HAS UNDERGONE RANGE OF MOTION TESTING OF THE CERVICAL REGION WITH
STANDARDIZED PROCEDURES, UTILIZING THE COMPUTERIZED ARTHROMETER BY TECHNOSTIX,
INC. TESTS WERE PERFORMED IN TRIPLICATE WITH THAT TEST DEMONSTRATING GREATEST
MOTION BEING RECORDED. IMPAIRMENT RATING SCORES HAVE BEEN APPROPRIATELY ROUNDED
TO THE NEAREST WHOLE NUMBER.

PROCEDURES OF THE CERVICAL REGION

FLEXION                                    EXTENSION
-----------------------------------        -----------------------------------
GREATEST RANGE            20 DEGREES       GREATEST RANGE            50 DEGREES
AVERAGE RANGE             60 DEGREES       AVERAGE RANGE             75 DEGREES
LOST MOTION               40 DEGREES       LOST MOTION               25 DEGREES
PERCENT LOST MOTION       67 PERCENT       PERCENT LOST MOTION       33 PERCENT
IMPAIRMENT WHOLE PERSON    4 PERCENT       IMPAIRMENT WHOLE PERSON    2 PERCENT
-----------------------------------        -----------------------------------

LEFT LATERAL FLEXION                       RIGHT LATERAL FLEXION
-----------------------------------        -----------------------------------
GREATEST RANGE            30 DEGREES       GREATEST RANGE            30 DEGREES
AVERAGE RANGE             45 DEGREES       AVERAGE RANGE             45 DEGREES
LOST MOTION               15 DEGREES       LOST MOTION               15 DEGREES
PERCENT LOST MOTION       33 PERCENT       PERCENT LOST MOTION       33 PERCENT
IMPAIRMENT WHOLE PERSON    1 PERCENT       IMPAIRMENT WHOLE PERSON    1 PERCENT
-----------------------------------        -----------------------------------

LEFT ROTATION                              RIGHT ROTATION
-----------------------------------        -----------------------------------
GREATEST RANGE            60 DEGREES       GREATEST RANGE            40 DEGREES
AVERAGE RANGE             80 DEGREES       AVERAGE RANGE             80 DEGREES
LOST MOTION               20 DEGREES       LOST MOTION               40 DEGREES
PERCENT LOST MOTION       25 PERCENT       PERCENT LOST MOTION       50 PERCENT
IMPAIRMENT WHOLE PERSON    1 PERCENT       IMPAIRMENT WHOLE PERSON    2 PERCENT
-----------------------------------        -----------------------------------

TOTAL OF WHOLE PERSON IMPAIRMENTS OF THE CERVICAL REGION: 11 PERCENT

TESTING PROCEDURES AND IMPAIRMENT RATING DETERMINATION CONFORM WITH THE STANDARDS
OUTLINED IN THE AMERICAN MEDICAL ASSOCIATION'S 'GUIDE TO THE EVALUATION OF
PERMANENT IMPAIRMENT. 3RD EDITION.'

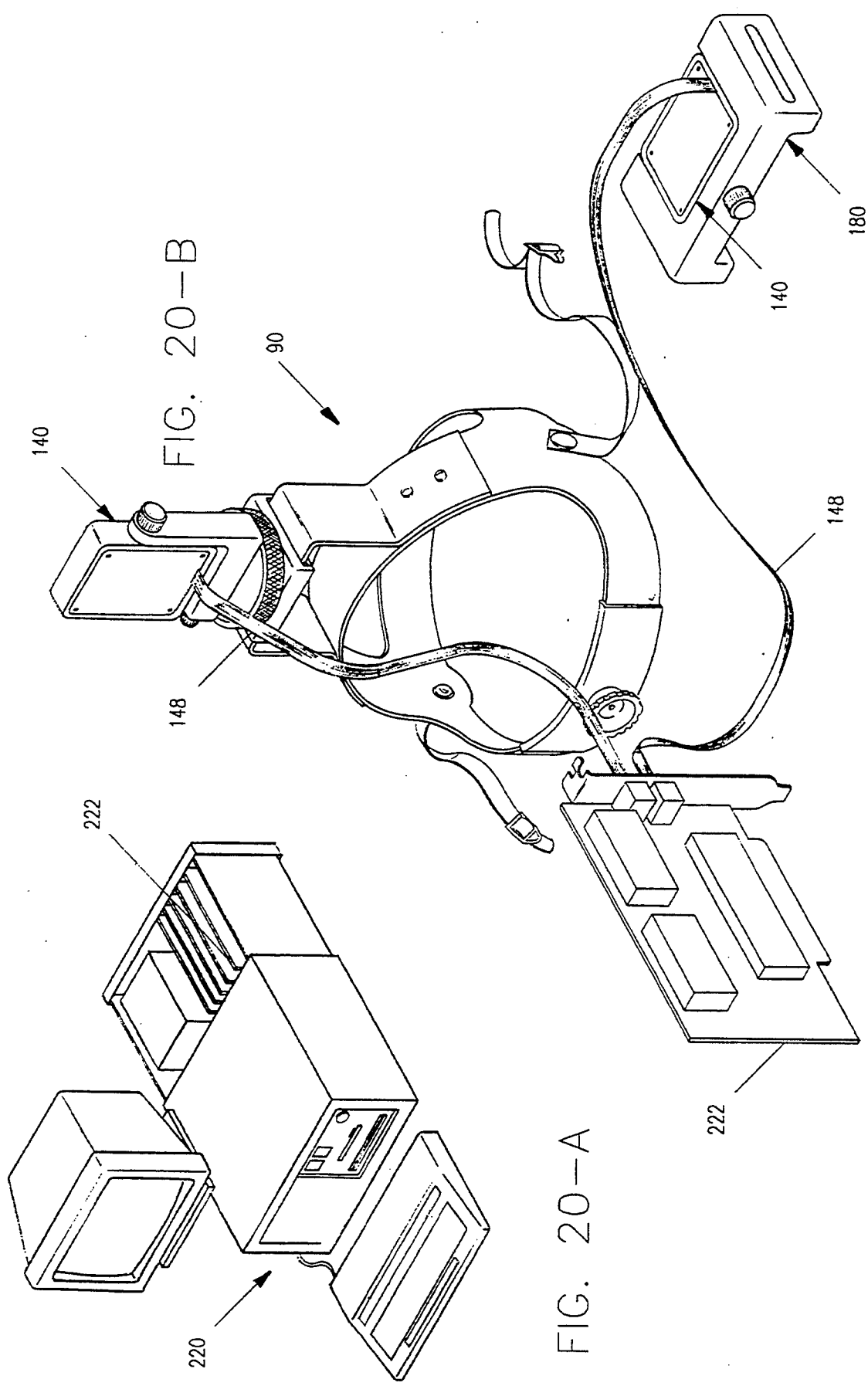

APPARATUS AND METHOD FOR DETERMINING
ANGLE OF INCLINATION AND RANGE OF
MOTION OF VARIOUS HUMAN JOINTS
THEREFROM

BACKGROUND OF THE INVENTION (a) Field of the Invention

The present invention relates to an apparatus and method used to determine angles of inclination and the range of motion of various human joints therefrom, such as, for example, cervical flexion. The apparatus of one preferred embodiment is e computerized arthrometer which is a stand-alone automated apparatus. Output can be provided to a printer for hard copy or to a computer for storage or further manipulation of data. Each sensor or inclinometer used in the preferred embodiment employs a pair of Hall effect transducers spaced about a rotating ring magnet. The voltage output from the transducers can be evaluated to accurately determine the angle of inclination. In another preferred embodiment, instead of the magnet and transducers, the sensors can include circular sensor having six capacitive sectors, each sector changing capacitance as the circular sensor is rotated. The six capacitance values are evaluated to determine the angle of inclination. Another embodiment incorporates the apparatus into readily available "personal computers" ("PCs"). By employing a pair of sensors for selected range of motion tests, measurement accuracy is increased by compensating for the effects of secondary motion, for example, compensating for forward or backward movement of the torso when measuring cervical flexion or cervical extension, respectively.

(b) Description of the Prior Art

There are known single inclinometers which can be determine and display the angle to which they are oriented. It is known to use multiple inclinometers, to position them at different locations on the body, and take readings from the multiple instruments. It is also known to measure an initial starting angle and an ending angle, with the angle therebetween being the range of motion. Further, inclinometers are known which display the angle difference between a first position and a second position.

For example, U.S. Pat. No. 4,912,662, to Butler et al., teaches an inclinometer having a capacitive sensing unit which provides varying capacitance depending upon the orientation of the inclinometer. By comparing the capacitance values to calibrated values stored in look-up tables, the angle of inclination can be determined.

Examples of available inclinometers which can display the difference in motion from a first position to a second position are the Autotilt digital inclinometer from the J-Tech Corporation and the Model SR360 Flexometer from SR Associates.

SUMMARY OF THE INVENTION

The present invention is for an apparatus and method used to determine the range of motion of various human joints, such as, for example, cervical flexion. The apparatus of one preferred embodiment is a computerized arthrometer which is a stand-alone automated apparatus. A main console assembly houses the processor, which interfaces with the operator or user, the output device, the first sensor attached to an adjustable cervical helmet worn by the person being tested by the operator, and the second sensor in a hand-held attachment. Alternatively, the apparatus sensors can be interfaced into a readily available "personal computer" ("PC").

Each sensor or inclinometer used in the preferred embodiment employs a pair of Hall effect transducers spaced about a rotating ring magnet. By placing the transducers about 120 degrees apart, the sinusoidal-shaped voltage output curve of one transducer is in a linear region when the sinusoidal-shaped voltage output curve of the other transducer is not in a linear region. To determine an inclination angle, the two transducer voltage outputs can be evaluated to determine which transducer voltage is in a more linear region of its sinusoidal-shaped curve. Interpolation is then accomplished by the processor using the more linear transducer voltage to accurately determine the angle of inclination.

In another preferred embodiment, instead of the magnet and Hall effect transducers, the sensors can include circular sensor having six capacitive sectors, three sectors on each of two parallel plates with the parallel plates having some fluid therebetween, each sector changing capacitance as the circular sensor is rotated causing movement of the fluid. To determine an angle of inclination, representations of the six capacitance values are sequentially determined and the two most linear are used.

By employing a pair of sensors (either being a Hall effect/magnet sensor or a capacitive sector sensor), for selected range of motion tests, measurement accuracy is increased by compensating for the effects of secondary motion, for example, compensating for forward or backward movement of the torso when measuring cervical flexion or cervical extension, respectively. Based on the sensor measurements, the raw measured data can be processed to not only convert the data into inclination angles, but to further analyze the data from both sensors to compensate for the secondary motion and to produce evaluation reports which are user friendly.

More particularly, one embodiment of the present invention comprises an apparatus for measuring an angle, including a support having a preselected zero degree point; a shaft rotatably connected to the support and protruding perpendicularly therefrom; a ring magnet connected to the shaft, the ring magnet having an outer cylindrical surface, the ring magnet being parallel to the support; a first Hall effect transducer, the first transducer connected to the support at a first preselected location and protruding perpendicularly therefrom, the first transducer being proximate said outer cylindrical surface of the ring magnet, the first transducer providing a first voltage output signal, the first voltage output signal representing a measurable first transducer magnetic field intensity; a second Hall effect transducer, the second transducer connected to the support at a second preselected location and protruding perpendicularly therefrom, the second transducer being proximate the outer cylindrical surface of the ring magnet, the second transducer providing a second voltage output signal, the second voltage output signal representing a measurable second transducer magnetic field intensity; and, means for evaluating the first voltage output signal and the second voltage output signal to determine an inclination angle, the inclination angle representing a measure of tilt of the support from the preselected zero degree point.

More particularly, a pair of these apparatuses for measuring an angle of this preferred embodiment can be employed with a cervical helmet and a hand-held assembly, and a programmed controller to permit conduct of a variety of range of motion tests and the calculation of related impairment results. Employing a pair of these apparatuses permits secondary motion to be discounted, thereby increasing more accurate representations of the tested ranges of motion. Alternative angle measuring apparatuses may be employed, such as one employing a six-sector capacitive sensor assembly.

For example, the apparatus for determining a range of motion can comprise a primary sensor producing at least one primary output signal representing an angle of inclination of the primary sensor; a secondary sensor producing at least one secondary output signal representing an angle of inclination of the secondary sensor; and, means for controlling the apparatus, the controlling means communicating with the primary sensor and the secondary sensor, the controlling means including means for initially evaluating the at least one primary output signal to determine a primary calibration angle of inclination and initially evaluating the at least one secondary output signal to determine a secondary calibration angle of inclination, means for evaluating the at least one primary output signal to determine a primary angle of inclination and evaluating the at least one secondary output signal to determine a secondary angle of inclination, means for comparing the primary angle of inclination and the primary calibration angle of inclination to determine a primary range of motion, means for comparing the secondary angle of inclination and the secondary calibration angle of inclination to determine a secondary range of motion, and means for comparing the primary range of motion and the secondary range of motion to determine an actual range of motion.

Even more particularly, the operator of the apparatus for determining range of motion employs a method comprising the steps of placing a helmet having a primary sensor on a head of a person to be tested; positioning the person to be tested in a neutral test position; selecting a range of motion test to be conducted; aligning the primary sensor for the selected test; aligning a secondary sensor in a desired body location of the person to be tested; calibrating a range of motion apparatus which is in communication with the primary and the secondary sensors; having the person to be tested move from the neutral test position to a range of motion measurement position; and, activating the range of motion apparatus to determine an actual range of motion.

BRIEF DESCRIPTION OF THE DRAWINGS

A better understanding of the present invention will be had upon reference to the following description in conjunction with the accompanying drawings, wherein:

FIG. 8 shows voltage response curves from two Hall effect transducers for a typical magnetic sensor rotated through 360 degrees;

FIG. 9 shows part of an output matrix for the magnetic sensor two voltage output levels for each one degree of magnetic rotation;

FIG. 10a shows a schematic of the circuit connectivity for the six sector capacitive sensor assembly of FIG. 4;

FIG. 10b shows the six sectors of the capacitive sensor in more detail;

FIG. 10c shows a basic astable circuit employing a 7555 timer integrated circuit chip and having a variable capacitor;

FIG. 10d shows a graph of capacitance versus 7555 timer output frequency as the variable capacitor of FIG. 10c is varied from 20 to 40 picofarads;

FIG. 13 shows a portion of an output matrix for the six sectors of the capacitive sensor and the ratio of the two most linear sectors in the shown portion;

FIGS. 18a-e depict sample cervical tests;

FIG. 19 is a sample of a printer output showing the results of cervical tests; and, FIGS. 20a-b show another preferred embodiment employing a personal computer.

DETAILED DESCRIPTION OF THE PREFERRED EMBODIMENT

Figure 1:
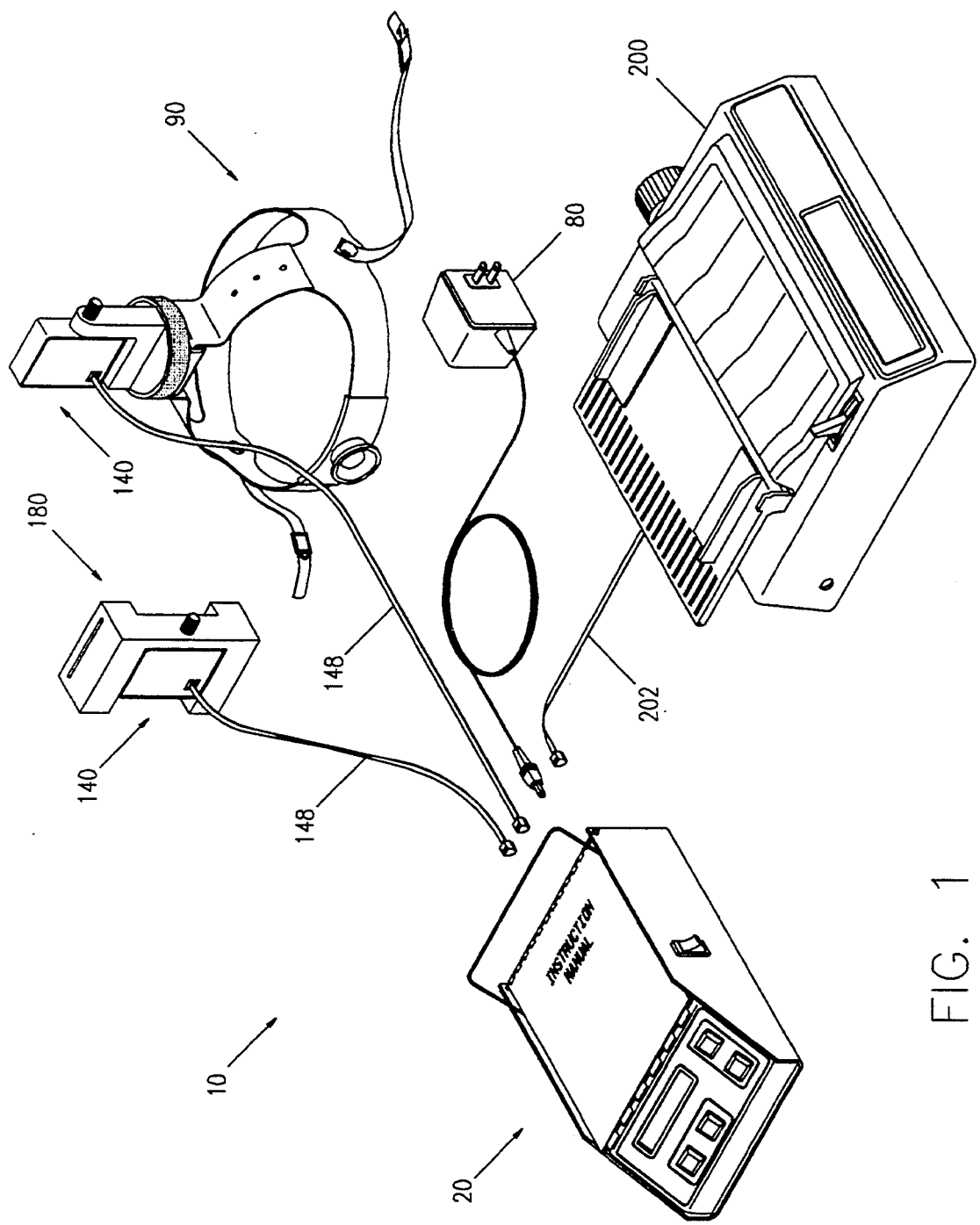
FIG. 1 shows the interconnectable components of the fully assembled apparatus of the preferred embodiment.

The stand-alone embodiment of the apparatus 10 for measuring range of motion is shown in FIG. 1. Apparatus 10, is shown including a main console assembly 20, a power supply and cord 80, a helmet sensor assembly 90 having an adjustable first sensor 140 attached thereto, a hand-held sensor assembly 180 having a second sensor 140 attached thereto, a pair of sensor/console interface cables 148, and a printer 200 having a printer/console interface cable 202.

Figure 3:
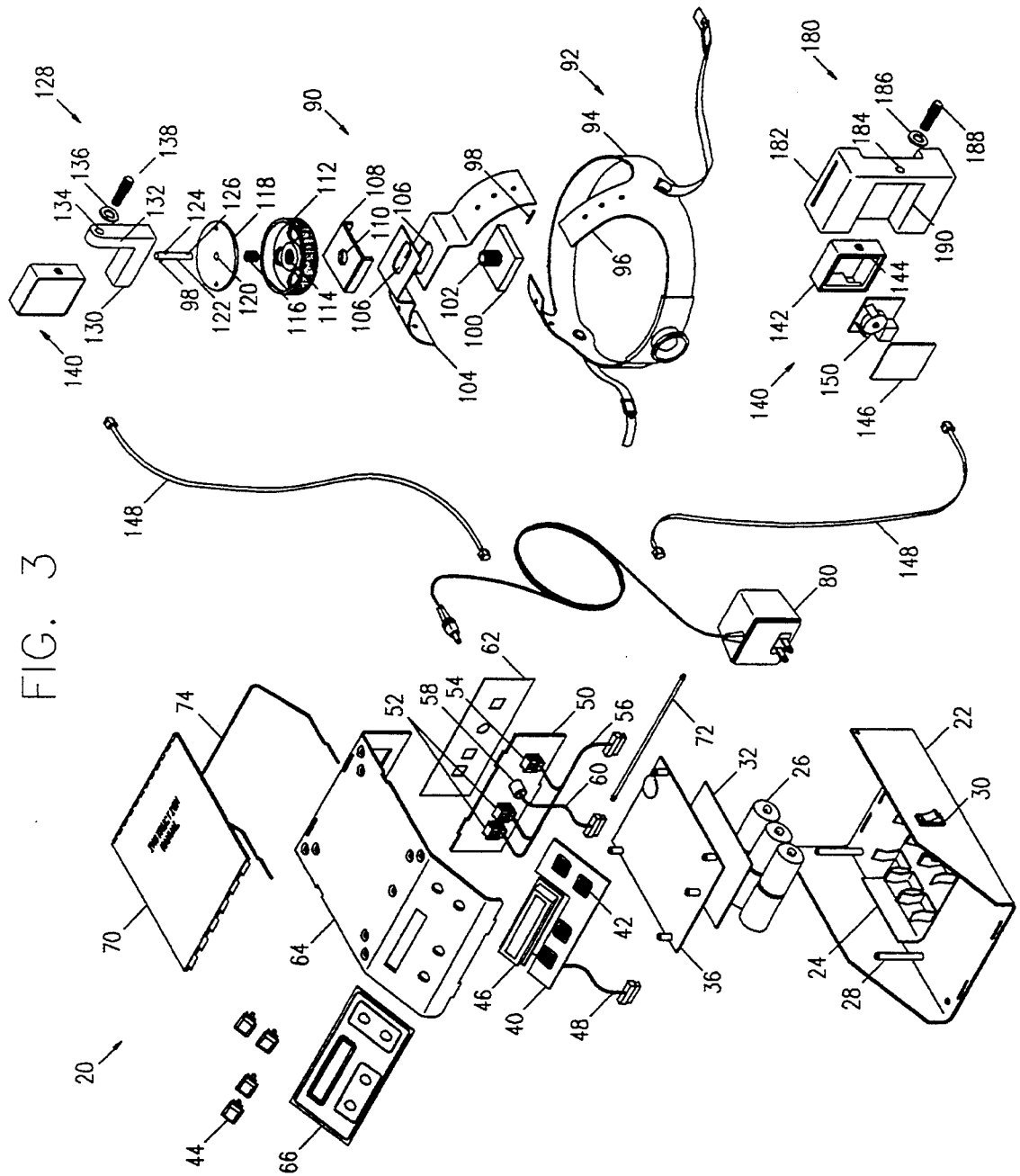
FIG. 3 shows an exploded view of the main console assembly, the cervical helmet sensor assembly, and the handheld sensor assembly of the apparatus of the preferred embodiment of FIG. 1, the sensors being magnetic sensors.

FIG. 3 shows an exploded view of the embodiment of FIG. 1 except for the printer 200 and its interface cable 202. Main console assembly 20 is shown having an outer bottom case 22, having battery pack receptacles 24 therein for receiving battery pack 26. Battery pack 26 is shown, for example, as containing six 1.5 volt rechargeable batteries connected electrically in series. External power to assembly 20 is provided by nine volt power supply and cord 80. The on/off power switch is designated by the numeral 30. For example, battery pack 26 can permit remote operation of the apparatus 10 for 3 to 4 hours with the battery being fully charged, if testing is to be completed where an external power source is unavailable or inconvenient.

Case 22 has circuit board standoffs 28 extending upward which provide support for the interface circuit board 32 and the controller circuit board 36. Interface circuit board 32 provides connectivity between the user input/output interface board the controller circuit board 36, the two sensors 140, and the printer 200. Board 32 input/output connectivity and board 32/board 36 connectivity is explained hereinafter with the discussion of FIG. 7.

For the preferred embodiment of FIG. 3, the controller circuit board 36 is a programmable miniature controller, sold by Z-World under the trademark "LITTLE GIANT" and having a Z180 processor with a 9.216 MegaHertz clock. The programming of the controller is discussed hereinafter, with reference to FIGS 14–17.

Figure 2:
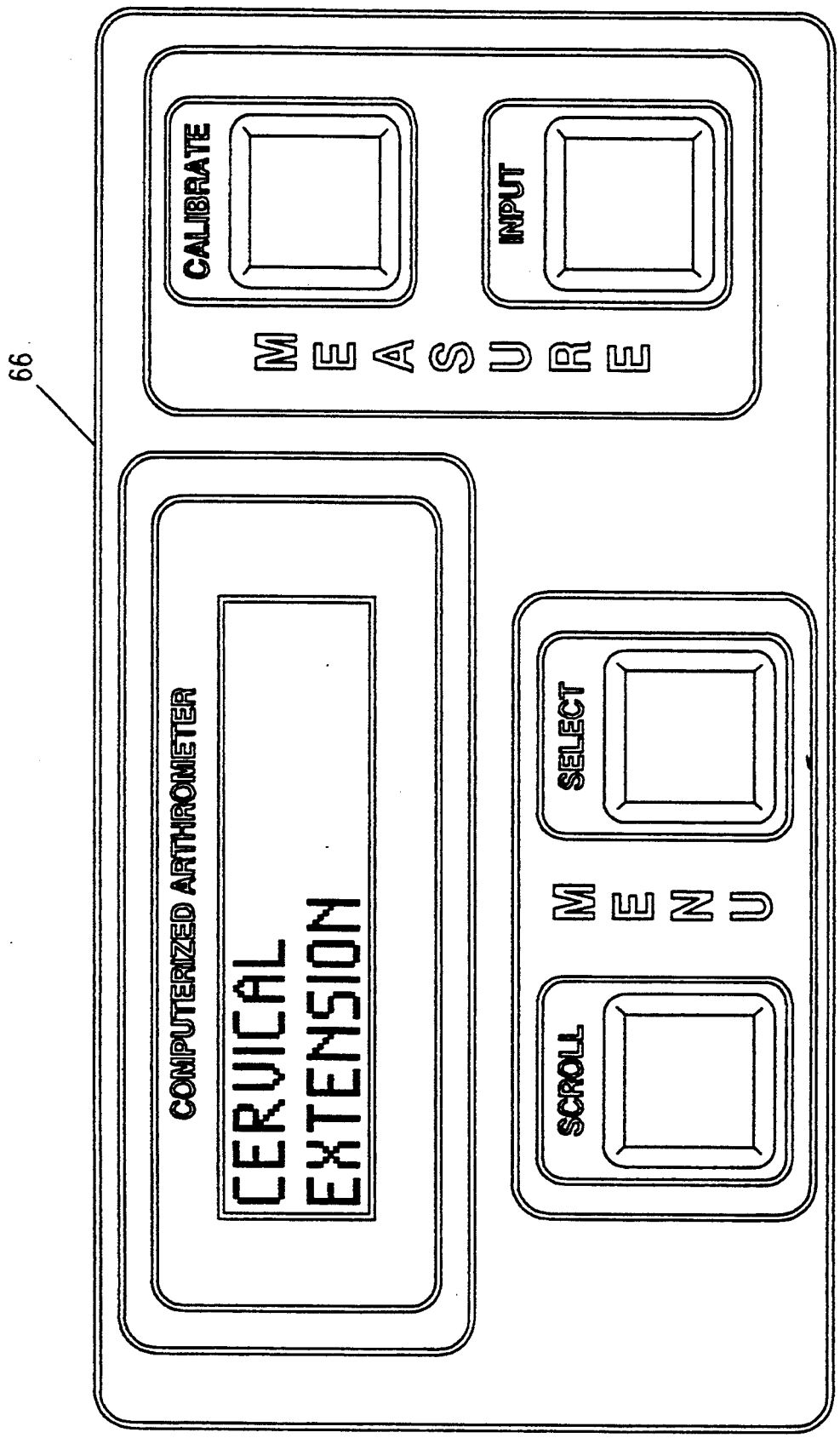
FIG. 2 shows the face of the main console assembly of the preferred embodiment of FIG. 1.

The user input/output interface board 40 is used by the user to select the desired operation and displays messages to the user. Control button interfaces 42 and control buttons 44 are touched by the user. LCD module 46 provides the display. Interconnect cable 48 interfaces user input/output interface board 40 and interface circuit board 32. Front face cover 66, seen in greater detail in FIG. 2, details the function of buttons 44.

Back plate 50 fits to the rear of outer bottom case 22 and provides the sensors, power, and output device connectivity. Each sensor input/output jack 52 receives one of sensor connecting cables 148. Cables 148 provide direct current operating voltage ($V_{cc}$) and ground from assembly 20 to sensors 140 and sensor information from sensors 140 to assembly 20. Printer output jack 54 connects to printer cable 202, or to another output device cable. Jacks 52 and 54 are connected to interface circuit board 32 by interconnect cable 56. Power supply and cord 80 connect to power input jack 58, which is connected to interface circuit board 32 by interconnect cable 60. Back plate 50 has a face cover designated by the numeral 62.

Outer top case 64 fits atop outer bottom case 22, back plate 50, and user input/output interface board 40. Front face cover 66 is received thereon. Also, for example, to aid the user when using apparatus 10, an instruction manual 70 can be provided. Secured to main console assembly 20 by booklet securing rod 72 and supported by booklet page rest 74, the user has easy access to information needed during operation of apparatus 10.

Figure 4:
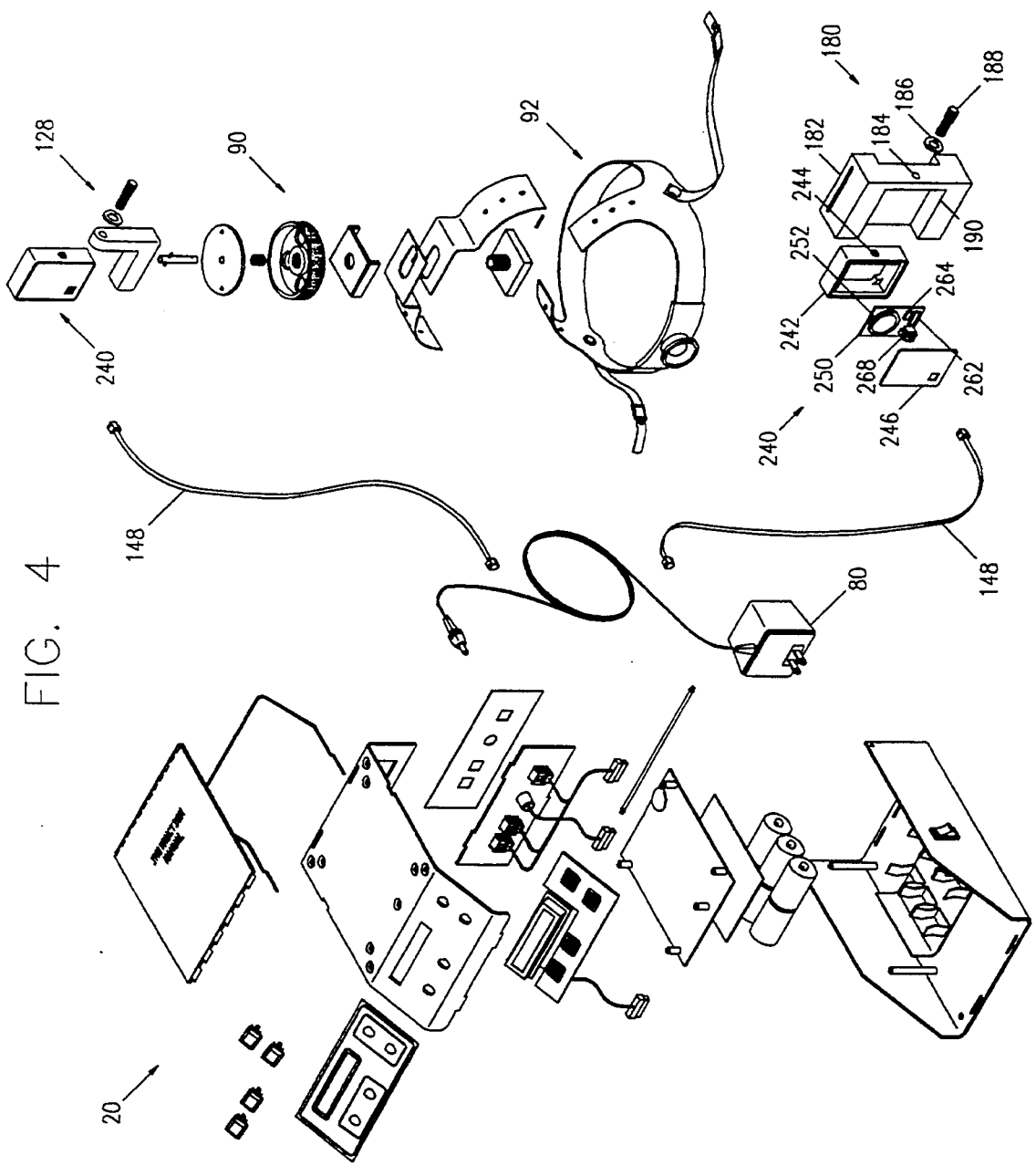
FIG. 4 shows an exploded view of the handheld sensor assembly of the apparatus of another preferred embodiment, the sensor being a six sector capacitive sensor.
Figure 7:
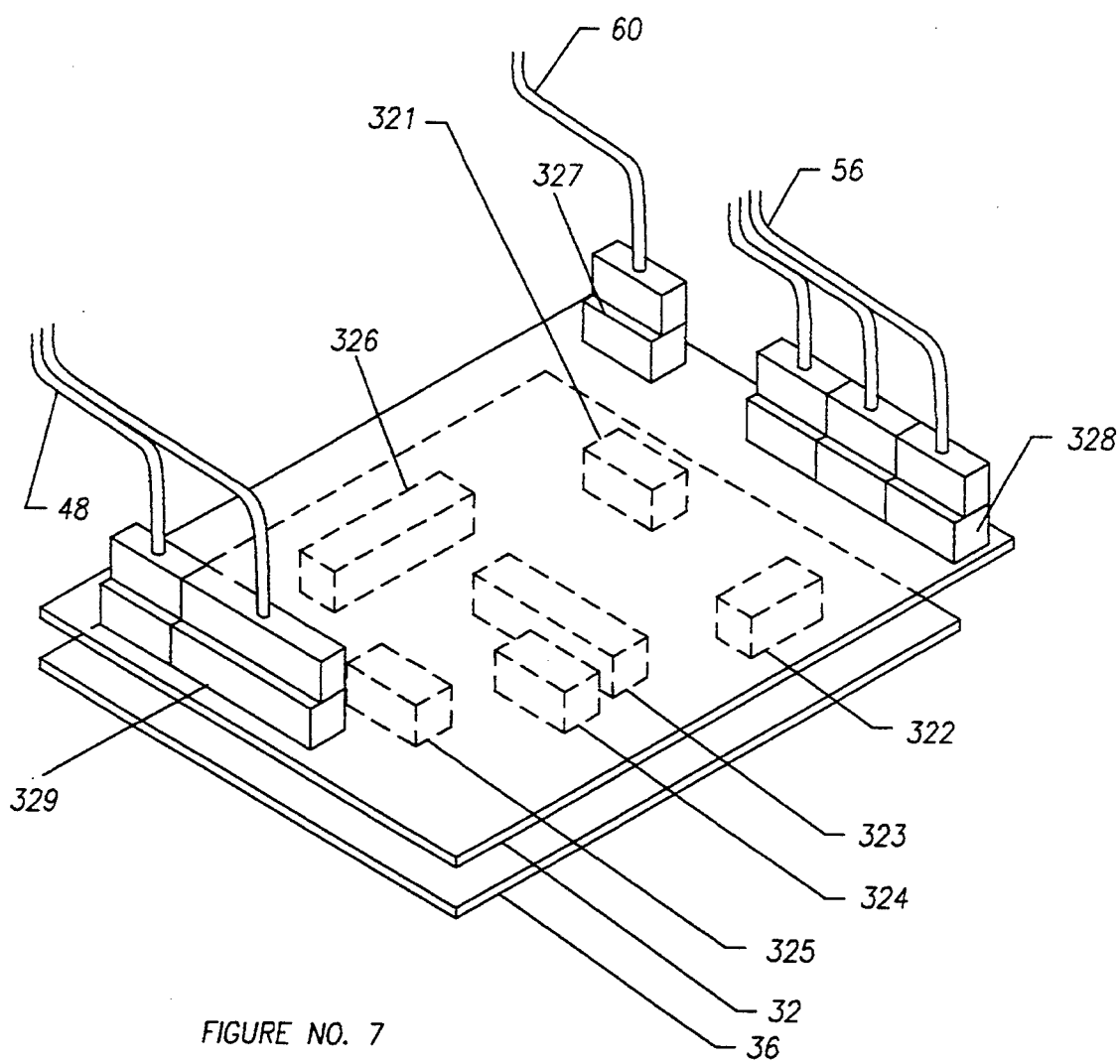
FIG. 7 depicts the interface circuit board connectivity to the controller board and the input/output connectivity to the interface circuit board from the two sensors and the printer, the power supply source, and the user input/output interface board of the apparatus of the preferred embodiment of FIGS. 1 and 3.

As shown in more detail in FIG. 7, interface circuit board 32 is depicted atop controller circuit board 36. For clarity, this is inverted from the exploded view of FIG. 3. One side of interface circuit board 32 contains plugs (321–326), shown in phantom, positioned to directly interface the "LITTLE GIANT" controller board 36. The other side of interface circuit board 32 contains jacks (327–329) which receive the plugs connected to the wires from the two sensors and the printer (56), the power source (60), and the user input/output interface board (48). Board 32 simply provides the necessary connectivity between the various components. For example, the 9 volts direct current from wire 60 is fed to jack 327 and to controller board 36 through power interface plug 321, to the sensors 140 (or 240 if the hereinafter explained embodiment of FIG. 4 is employed) through jack 328, and to the user input/output interface board 48 through jack 329. Data counter interface plug 322 provides input square wave timing pulses from the capacitive sensors 240, explained hereinafter, to a counter timer on board 36. Analog to digital converter plug 326 provides input from the Hall effect transducers 164 and 166 of sensors 140 to the analog/digital subsystem of board 36. Input/output interface plug 323 provides the output from control buttons 44 to board 36. Display interface plug 324 provides output information from board 36 to liquid crystal display module 46. Serial interface plug 325 provides connectivity from board 36 to printer 200.

With reference back to FIG. 3, helmet sensor assembly 90 is adjustable and straps to a patient's head. Assembly 90 supports the sensor 140 which provides primary inclination information. Handheld sensor assembly 180 supports the sensor 140 which provides secondary inclination information.

Helmet sensor assembly 90 includes a helmet 92 having an adjustable strap 94 which extends around a patient's head and a pair of sensor straps 96 which extend toward the top of a patient's head to support sensor 140. Connected to straps 96 are a pair of adapting straps 104, each having a bore 106 therethrough. Mounting block 100 has a hollow post 102 extending upward therefrom. Post 102 is received upward through bores 106. Securing block 108 having a bore 110 therethrough fits atop adapting straps 104 and receives post 102. Securing flange 112 having a spring bore 114 therethrough sits atop securing block 108 and receives post 102.

Coil spring 116 is received in spring bore 114. Securing flange lid 118, having a bore 120 therethrough, is placed atop securing flange 112. Bore 120 is sized approximate the hollow portion of post 102 of mounting block 100. With mounting rod 122 having a pin 98 inserted through an upper bore 124 placed downward through bore 120 of securing flange lid 118, an L-shaped helmet sensor mount 128 is screwed to the top of securing flange lid 118. Hollow post 102, bores 106 in adapting straps 104, bore 110 in securing block 108, spring bore 114 in securing flange 112, coil spring 116, and bore 120 in securing flange lid 118 are axially aligned and a mounting rod 122 is inserted therethrough. Another securing pin 98 is then inserted through a lower bore 126 in mounting rod 122 to rotatably secure the L-shaped helmet sensor mount 128 to the helmet assembly 90. This connectivity permits the L-shaped helmet sensor mount 128, and hence the sensor assembly 140 attached thereto, as described hereinafter, to be rotated about the axis of mounting rod 122 to properly align the sensor 140 for proper testing of a patient wearing the helmet sensor assembly 90.

L-shaped helmet sensor mount 128 has a horizontal arm 130 and a vertical arm 132. Arm 132 has a bore 134 therethrough. As explained hereinafter, washer 136 and 138 can be used in conjunction with bore 134 to attach sensor assembly 140. It is noted that mounting rod 122 and screw 138 are in transverse alignment. This permits adjustment of sensor about the axes of both rod 122 and screw 138 to, therefore, adjust the sensor for any plane of motion.

Sensor assemblies 140 of the preferred embodiment of FIGS. 1 and 3 each employ a pair of Hall effect transducers 164 and 166 positioned about a one pole pair ring magnet 162. Sensor assemblies 140 are shown in greater detail in FIGS. 5 and 6 and their output is discussed hereinafter with FIGS. 8 and 9.

As previously mentioned, a primary sensor assembly 140 is pivotally attached to vertical arm 132 of L-shaped helmet sensor mount 128 and a secondary sensor assembly 140 is attached to handheld sensor assembly 180. Sensor assembly 140 is shown having a housing 142 having a threaded bore 144 therethrough. Bore 144 is used to pivotally attach primary sensor assembly 140 to arm 132 using screw 138. Handheld sensor assembly 180 has a housing 182 which includes a sensor receptacle 190. A bore 184 passes through housing 182 to receptacle 190. Washer 186 and screw 188 are used to fixedly secure secondary sensor assembly 140 into receptacle 190 by inserting screw 188 having washer 186 inserted thereover into bore 184 through housing 182 and into bore 144 of secondary sensor assembly 140.

Figure 5:
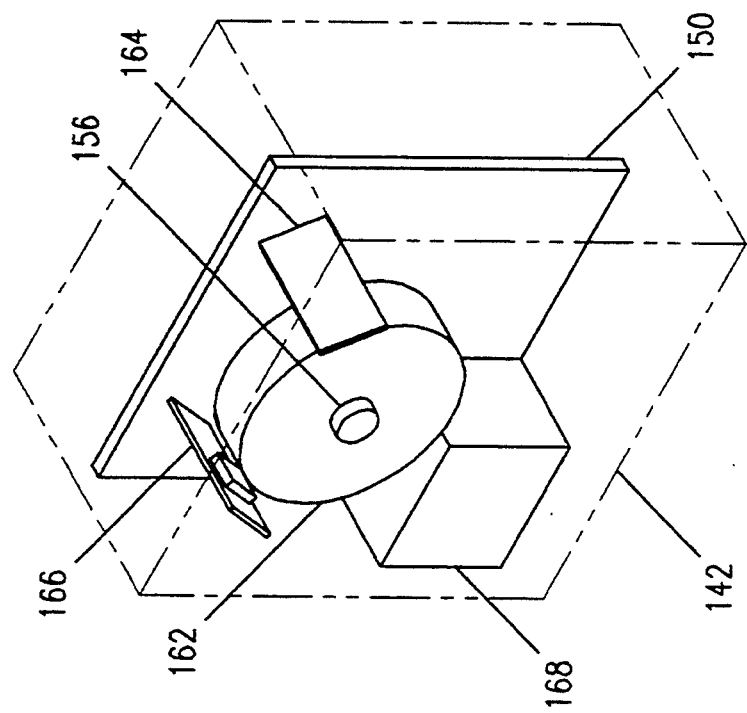
FIG. 5 shows a front perspective view of the magnetic sensor assembly of FIGS. 1 and 3.
Figure 6:
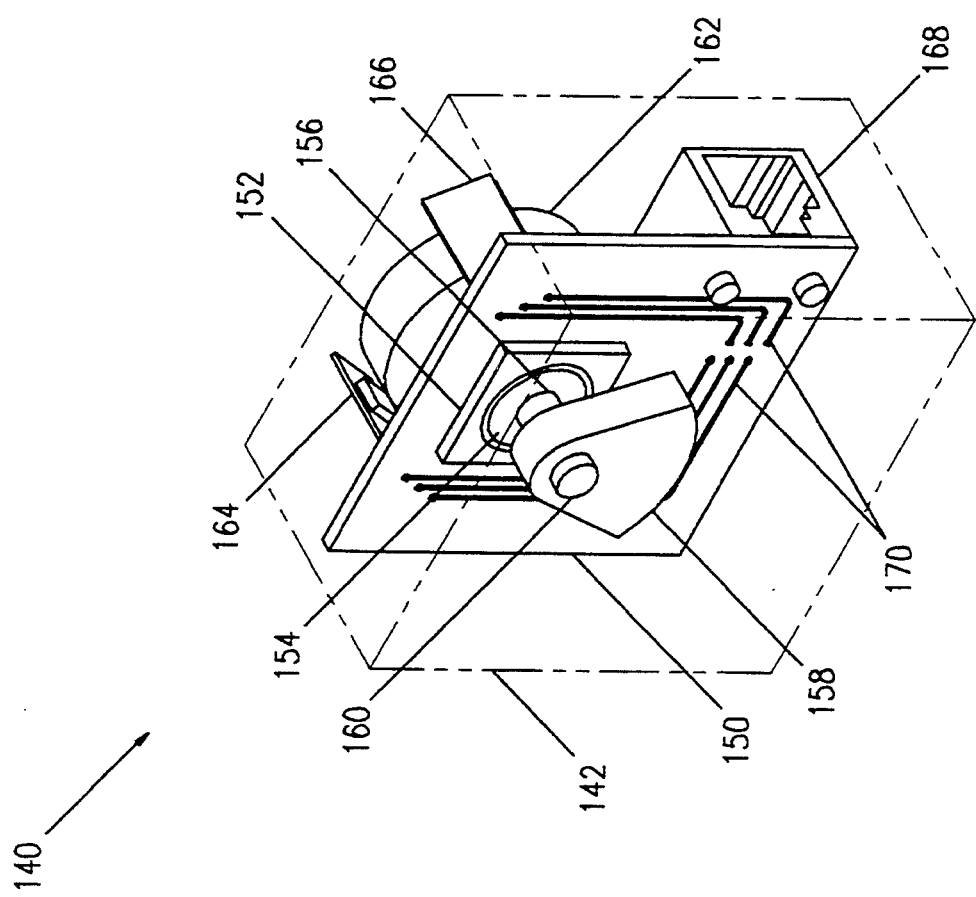
FIG. 6 shows a rear perspective view of the magnetic sensor of FIG. 5.

Each sensor 140 housing 142 contains a circuit board support 150 and a connector 168. Lid 146 attaches to housing 142. As shown in FIGS. 3, 5, and 6, circuit board 150 is quadrilateral-shaped support, for example, 1½ inch by 1½ inch, having a reinforcing mounting block 152 attached on one side. Block 152 and board 150 have a bore 154 therethrough. Bore 156 has rotating shaft assembly 156 inserted therethrough, the shaft assembly 156 being perpendicular to board 150. Shaft assembly 156, for example, extends about ⅜ inch from each side of board 150. A pendulum weight 158 of, for example, a triangular or bell shape, has a bore 160 therethrough. Using bore 160, weight 158 is attached to one end of shaft assembly 156. A one pole circular ring magnet 162 having a central bore is attached to the other end of shaft assembly 156, this being on the other side of board 150 from weight 158.

A first Hall effect transducer 164 and a second Hall effect transducer 166 are attached to board 150 and transverse thereto. Transducers 164 and 166 are also parallel to shaft assembly 156 and circumferentially aligned with ring magnet 162. It is noted, for example, that in this preferred embodiment, transducers 104 and 166 are spaced about 120 degrees apart, using shaft assembly 156 as a center reference. As is explained hereinafter, no matter the polar alignment of the magnet with respect to transducers 164 and 166, this spacing ensures the voltage output of at least one of the transducers 164 and 166 will be in a linear range. Connector 168 receives a connecting cable 148 which is then attached to proper input/output jack 52 of assembly 20. Connector 168 is electrically tied to board connectivity 170. Board connectivity 170 provides $V_{cc}$ and ground to each transducer 164 and 166 and provides a path for the direct current voltage output signal from each transducer 164 and 166. As mentioned, the output signals from the magnet/Hall effect transducer sensors assemblies 140 are passed to the analog to digital converter subsystem of the "LITTLE GIANT" controller 36 for sampling by controller 36 and evaluating to determine angles of inclination.

As seen in FIG. 8, as the magnet 162 is rotated through 360 degrees of rotation the output signal of each transducer 164 and 166 varies in proportion to the intensity of the magnetic field to which each transducer 164 and 166 is exposed. These output voltage curves are generally of a sinusoidal shape, having non-linear peaks and valleys and linear portions therebetween. The output curves of FIG. 8 represent measured data from actual Hall effect transducers configured as shown in FIGS. 5 and 6. FIG. 8 shows that with the about 120 degree spacing between transducer 164 and 166, output 1 from transducer 164 is in a linear range when output 2 from transducer 166 is in a non-linear range. Also, output 2 from transducer 166 is in a linear range when output 1 from transducer 164 is in a non-linear range. The controller 36 has the measured data for each one degree of rotation stored in a look-up matrix. The controller 36 is programmed, as is explained hereinafter, to select the transducer 164 or 166 output voltage which is in the most linear range and interpolate from the data in the look-up matrix for that most linear transducer 164 or 166 to determine the angle of inclination.

FIG. 9 shows a look-up matrix which would be stored for the curves of FIG. 8 from 45 degrees to 90 degrees of rotation. It is noted generally that output 2 from transducer 166 is the most linear over this range. To demonstrate this, for example, it is noted that the voltage change from 45 to 46 degrees for output 1 is only 0.002 volts, but for output 2 is 0.031 volts. Between 89 and 90 degrees, output 1 changes 0.015 volts and output 2 changes 0.040 volts. Therefore, over this range, the output 2 signal would be used for interpolation. To illustrate, assume that output 1 was measured at 6.537 volts and output 2 was measured at 3.097 volts. Looking at FIG. 8, the angle of inclination can only be around 50 degrees. Looking at the matrix of FIG. 9 shows that the angle of inclination must be between 50 and 51 degrees. Over this degree, output 1 changes only 0.005 volts and output 2 changes 0.034 volts. The output 2 signal is therefore used for interpolation and 3.097 volts is 0.017 volts above the output 2 50 degree voltage of 3.080 volts and 0.017 volts below the output 2 51 degree voltage of 3.114 volts. Therefore, the angle of inclination would be 50.5 degrees. If only one degree accuracy is desired, interpolation as described could still be accomplished, 0.5 degree could be added to the result, with the result truncated to eliminate any decimal, thus determining the angle of inclination to the nearest degree.

FIGS. 4, 10a-d, 11, 12, 13, and 17 relate to another preferred embodiment employing capacitive sensor assemblies 240, instead of the magnet/Hall effect transducer sensor assemblies 140. As with each assembly 140, each assembly 240 includes a housing 242, a bore 244, a lid 246, a jack 268, and a circuit board 250. Primary sensor assembly 240 is rotatably connected to L-shaped sensor mount 128, just like a sensor 140. Secondary sensor 240 is secured in sensor receptacle 190 of handheld sensor assembly 180 just like a sensor 140.

As seen in FIGS. 4 and 10a-b, circuit board 250 includes a capacitive sensor 252 having a pair of spaced apart parallel plates 254, each plate having three 120 degree sectors 258. Plates 254 are contained by a grounded case 253. The space between plates 254 is partway filed with a conductive fluid 256. It is noted that the 120 degree sectors 258 of one of plates 254 are off-set 60 degrees from the 120 degree sectors 258 of the other plate 254. Each of the six sectors 258 have a lead 260 electrically connecting the sector to an input of a 4051 multiplexer integrated circuit 262. Based on the fluid 256 position, the output from each sector 258 represents a capacitance through the sector and the fluid, if any, to the case ground. As the sensor 252 is rotated, the fluid 256 changes position and the output from the six sectors changes. A 7555 timer chip 264 and a precision resistor R1 are employed with the multiplex chip 262 to determine the angle of inclination of the sensor 252.

Before explaining the operation of the multiplex chip 262 and timer chip 264, reference is made to FIGS. 10c–d. FIG. 10c shows a basic astable circuit employing a 7555 timer integrated circuit chip, a fixed 10 Megohm resistor R1 and a variable capacitor C1. This circuit produces an output train of timing cycles having a period T1 which varies as C1 is varied. Frequency is 1 divided by period T1. FIG. 10d shows a graph of the output frequency of the circuit of FIG. 10c as C1 is varied from 40 picofarads to 20 picofarads. With C1 equal 40 picofarads, 1/T1 is 1.8 kilohertz. Thus T1 is approximately 0.55 milliseconds. With C1 equal 20 picofarads, 1/T1 is 3.6 kilohertz. Thus T1 is approximately 0.27 milliseconds. The relationship between C1 and frequency is linear.

With reference now to FIGS. 10a–b and 11–13, the operation of the multiplex/timer circuit on the circuit board 250 of sensor assembly 240 is explained. The multiplex/timer circuit output, as well as the multiplex 262 BCD addressing inputs are electrically connected to the "LITTLE GIANT" controller 36. When controller 36 is asked to measure an angle of inclination, the controller 36, through the BCD addressing inputs of multiplex 262, sequentially samples the six sensor sectors 258. Each sector's capacitance is dependent upon the position of the fluid 258 between the parallel sector plates 254. The software of this preferred embodiment is, for example, designed to measure the time it takes for the 7555 timer 264 to produce 36 clock pulses, skipping the first clock pulse for rise time of the capacitor for each of the six sectors 258. These six time measurements are then used to determine the angle of inclination.

Figure 11:
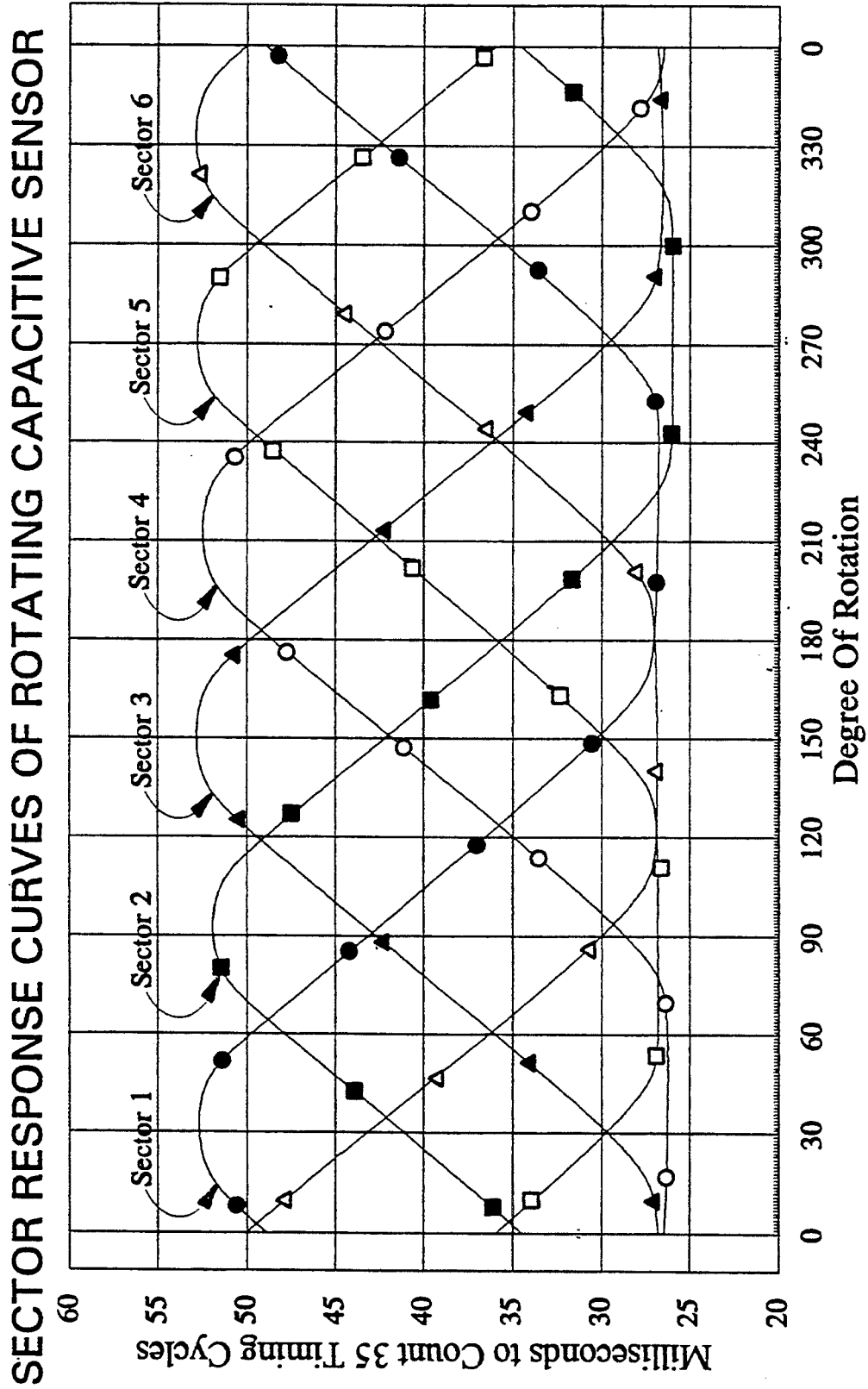
FIG. 11 shows a time response curve for a typical six sector capacitive sensor assembly through 360 degrees of rotation.

FIG. 11 shows typical response curves for the six sectors 258 of a sensor assembly 240 as the assembly 240 is rotated through 360 degrees. These curves for each sector are generally sinusoidal-shaped. From FIG. 10b, it is seen that the geometrical spacing of the sectors 258 is such that the arc midpoints of the six sectors are spaced about every 60 degrees with relation to case 253. The curves of FIG. 11 depict this geometric relationship, with the sector curves having their maximum timing about every 60 degrees of rotation.

Figure 12:
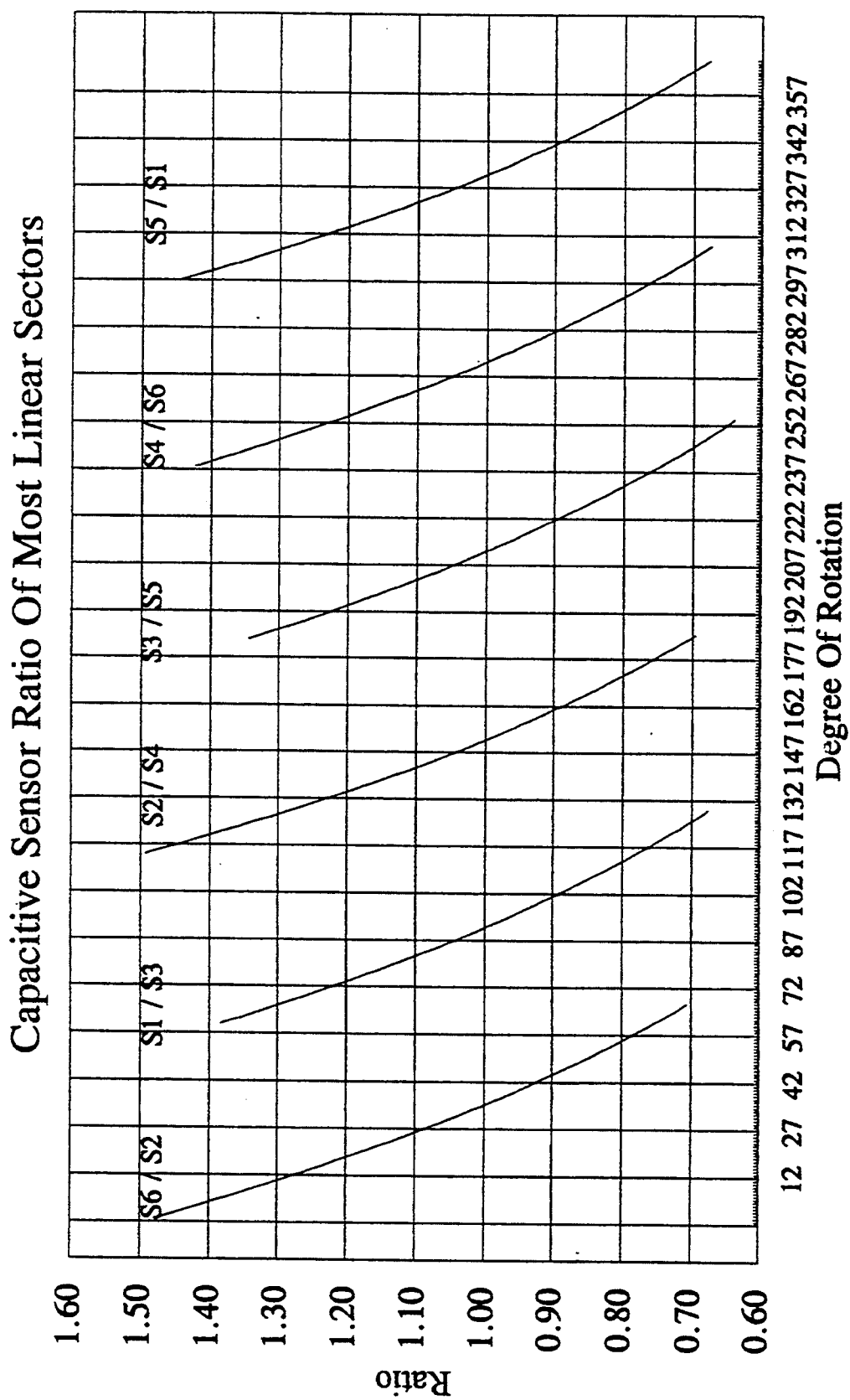
FIG. 12 shows a graph depicting the ratio of the appropriate two of the six capacitive sensor sectors of FIG. 11 used to determine the inclination angle.

While many methods could be employed to calculate an inclination angle, the program of this preferred embodiment looks to the sector with the longest time measurement to decide which 60 degree portion the angle is in. Then, similarly to the magnet/Hall effect transducer sensor assembly 140, a matrix is referred to determine the angle of inclination. It is noted that, for each 60 degree portion, the timing outputs of two of the six sensors change in a nice linear relationship. For example, for the 60 degree portion of the curves of FIG. 11 when sector 1 produces the longest time output (from about 3 degrees to about 63 degrees), the timing outputs of sectors 2 and 6 provide nice linear change. FIG. 12, at the left hand side from about 3 to 63 degrees, shows the ratio of the time for sector 6 to produce 35 pulses divided by the time for sector 2 to produce 35 pulses. From FIGS. 11 and 12, it is similarly seen that when sector 2 has the longest time to produce 35 pulses, sectors 1 and 3 are the most linear; when sector 3 has the longest time to produce 35 pulses, sectors 2 and 4 are the most linear; when sector 4 has the longest time to produce 35 pulses, sectors 3 and 5 are the most linear; when sector 5 has the longest time to produce 35 pulses, sectors 4 and 6 are the most linear; and, when sector 6 has the longest time to produce 35 pulses, sectors 5 and 1 are the most linear. For each one degree of rotation, the ratio of the two most linear sectors is stored in a lookup matrix. FIG. 13 shows a sample of the time measurements for each sector from 358 degrees to 31 degrees and the ratio of sectors 6 and 2. The program of this preferred embodiment, when making a determination of the angle of inclination first looks to the longest measured time for 35 pulse cycles to determine which two sectors times should be ratioed. For example, if the sector 1 time measurement is the longest at 51.862 milliseconds for 35 pulse periods, the time for sector 6 is divided by the time for sector 2, yielding, for this example, a ratio of 1.229635. Controller 36 refers to the 3 to 63 degree portion of the lookup matrix and sees that the ratio of sector 6 to sector 2 for 15 degrees is 1.23603 and for 16 degrees is 1.22324, the ratio 1.229635 being therebetween. Controller 36 uses these ratios to interpolate, giving a measured angle of inclination of 15½ degrees. As with sensor assembly 140, if inclination only to the nearest degree is required, 0.5 degree can be added to the interpolated result and the decimal truncated.

FIGS. 18a–e show a person wearing helmet sensor assembly 90 having a primary sensor 140 thereon and also shows the employment of a secondary handheld sensor assembly 180 having a secondary sensor 140 thereon. The sensors 140 are positioned depending on the test to be performed. The circuit boards 150 are always positioned to lie is a vertical plane. Also, for example, using FIGS. 18a–b as a guide, the person is being tested for cervical flexion and extension, respectively. Assuming the person is aligned so that his head movement is to the north or south, the sensors 140 are aligned so that the circuit boards 150 lie in the vertical north/south plane of motion. The same applies if a capacitive sensor assembly 240 is employed.

As seen in FIGS. 18a–b, the purpose of the primary sensor 140 is to measure the respective forward and reverse tilt of the head. As the person's neck and spine move in concert and not at one specific point, the purpose of the secondary sensor 140 is to make any necessary adjustment to the primary sensor 140 measurement to eliminate the effects of secondary motion by the person. In FIGS. 18d–e, the person is tilting his head from the neutral upright position (FIG. 18d) to the right (FIG. 18e) to determine right lateral flexion. Secondary sensor assembly 180 is positioned to measure the right tilt of the spine to eliminate this secondary motion. In FIG. 18c, the person is laying flat on a table and is twisting his neck to the right to measure right cervical rotation. As the spine may only twist during this measurement, no secondary motion need be eliminated. Therefore, the secondary sensor assembly is shown placed on the table beside the person being tested. The controller 36 is programmed, for this cervical rotation test, to only use input from the primary sensor assembly 140 attached to helmet assembly 90.

FIG. 19 depicts a typical data output sheet from a test of a person's cervical range of motion and the calculations of impairment which can be performed and produced on printer 200. It is seen that cervical flexion, extension, left and right lateral flexion, and left and right rotation have been measured. Using standards from the American Medical Association, cervical impairment has been calculated. To help ensure accuracy, it is noted that the tests have been repeated at least three times, with the greatest range of motion reported. It is also noted that the at least three tests must yield similar results, for example, within a ten percent range or no more than a five degree difference.

Figure 14:
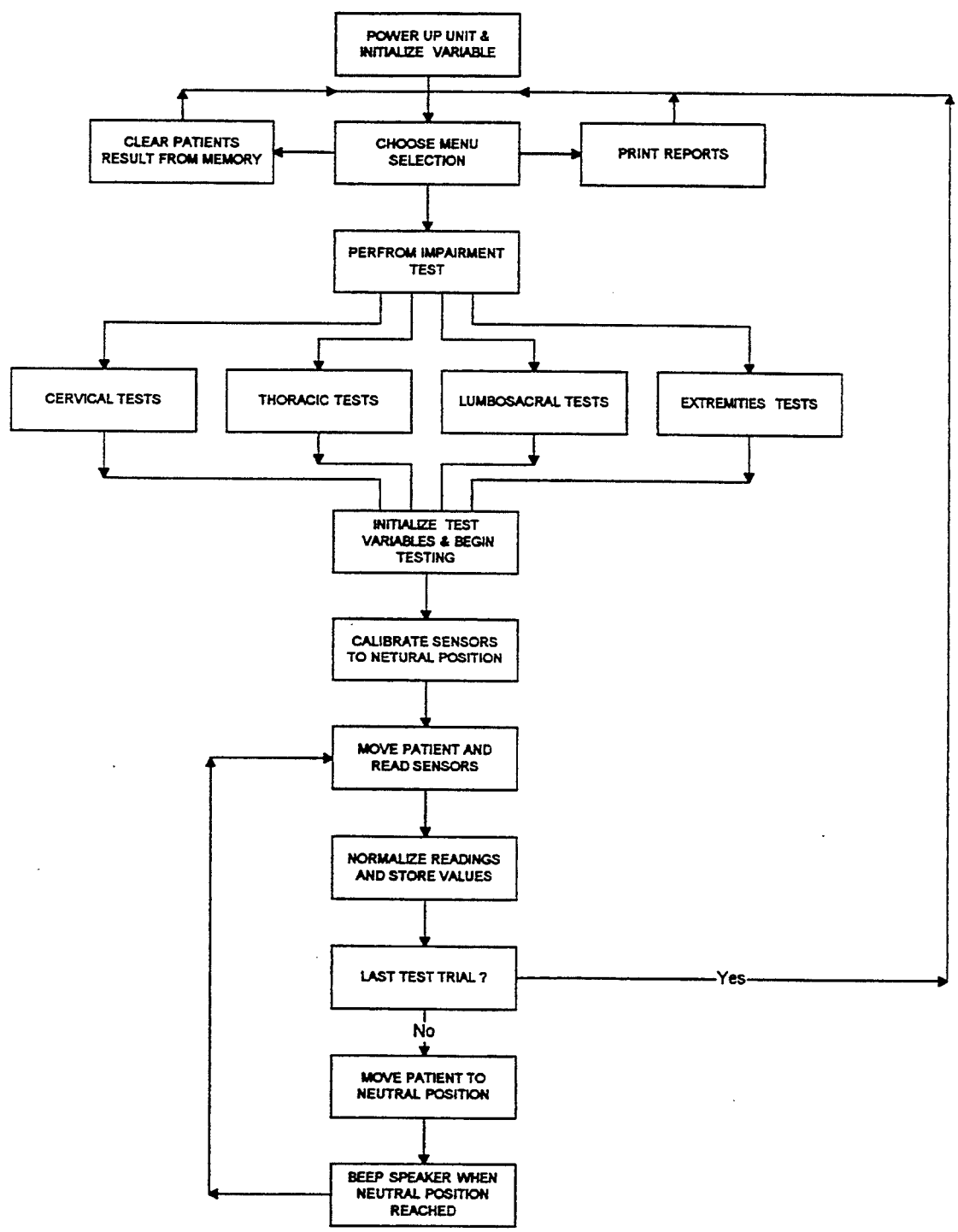
FIG. 14 shows a general flow chart of the operation of the apparatus of the preferred embodiment of FIG. 1.
Figure 15:
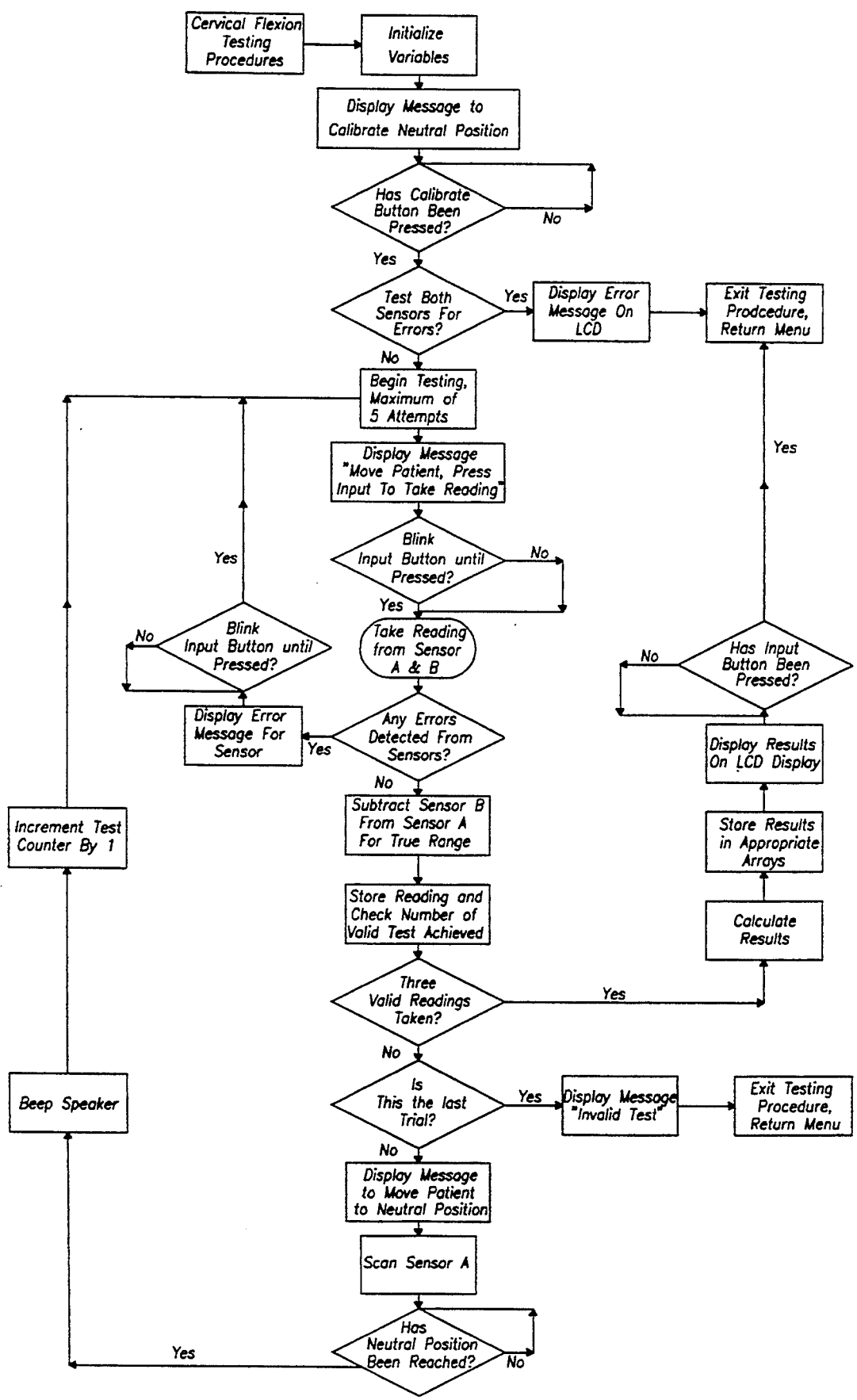
FIG. 15 shows an expanded flow chart for measuring cervical flexion.
Figure 16:
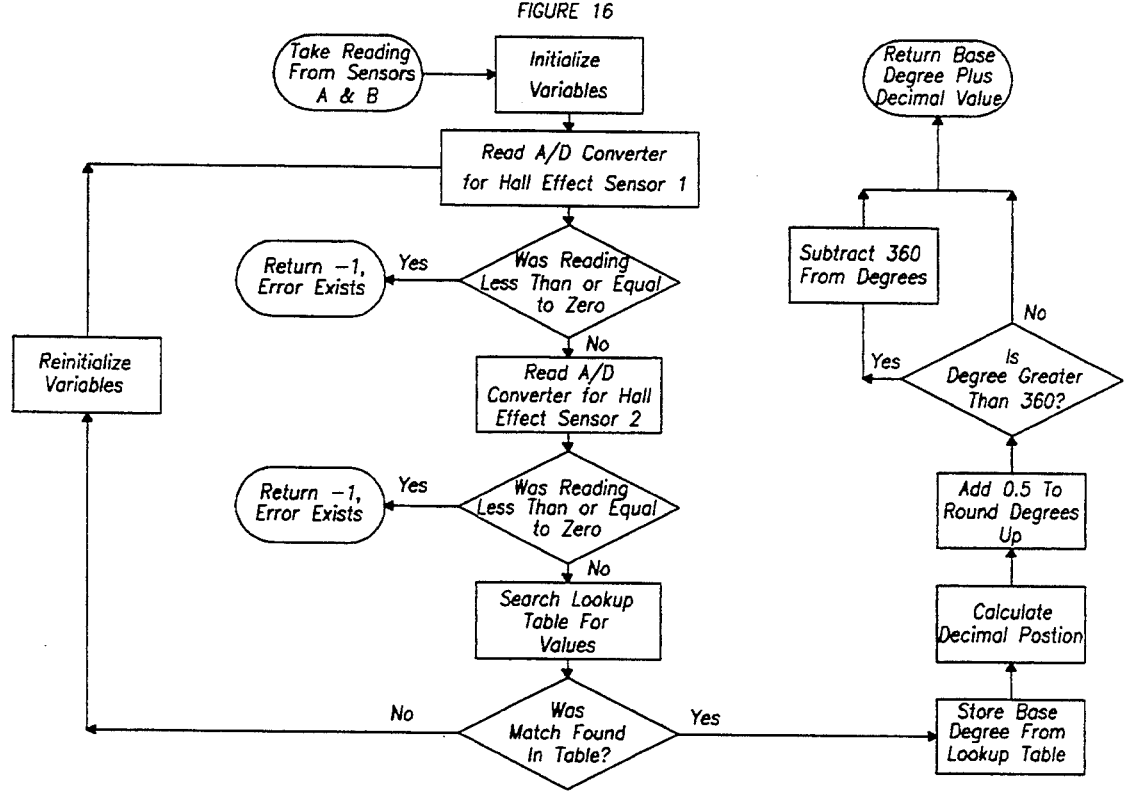
FIG. 16 shows an expanded flow chart of the flow chart of FIG. 15 for taking readings from the magnetic sensors.
Figure 17:
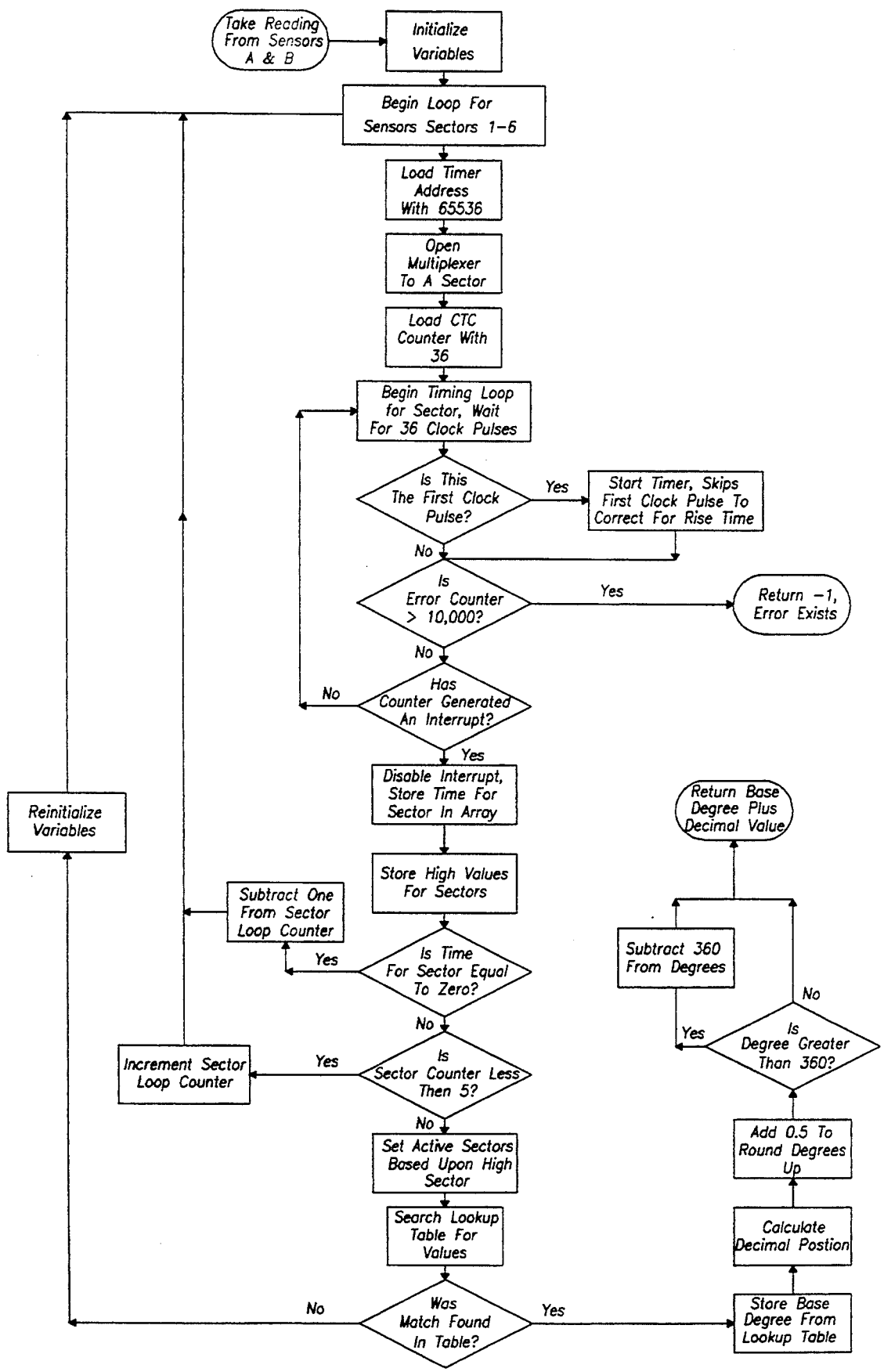
FIG. 17 shows an expanded flow chart of the flow chart of FIG. 15 for taking readings from the six sector capacitive sensors.

Various flow charts which permit the "LITTLE GIANT" controller 36 to perform the various tests and present the results are shown in FIGS. 14-17. FIG. 14 depicts a general flow chart from power up through test selection and testing and reporting. FIG. 14 shows that a person can have tests of the cervix, thorax, lumbar, and extremities selected, for example. FIG. 15 provides a more detailed flow chart assuming that a test of a person's cervical flexion has been selected. Toward the center of FIG. 15, a block is labeled "Take Reading from Sensor A & B". FIG. 16 expands on this block if a magnet/Hall effect transducer sensor assembly 140 is employed. FIG. 17 expands on this block if a capacitive sensor assembly 240 is employed.

In addition to being able to refer to the handy instruction manual 70 atop main console assembly 20, interface with the apparatus 10 by the operator is through the main console assembly 20. The operator responds to the messages displayed on LCD module 46. The operator uses the scroll and select menu control buttons 44 to select the desired test. Then, the operator has the person being tested move when appropriate and presses the appropriate calibrate and input measurement control buttons 44 to step through the desired testing sequences.

It is noted that with the primary and secondary sensors 140 and/or 240 properly positioned and with the person to be tested in the proper neutral position the controller 36 determines the angle of inclination for the primary and secondary sensors at this neutral position when the operator presses the calibrate control button 44. This neutral position is "remembered" so that the person being tested, when returned to the neutral position, hears a beep to indicate proper positioning to repeat the test. As previously mentioned, the desired test is to be completed at least three times and the results must be closely related or the test is considered invalid. Having the same neutral position as a starting point for all test repetitions helps test repeatability, rather than recalibrating for each test repetition. After calibration of the neutral position the person being tested is told how to move. When the person moves, the operator presses the input control button 44 and controller 36 takes the readings from sensors 140 or 240 and calculates the angles of inclination using the linear sensor relationships and the interpolation and truncation techniques previously described. This flow is shown for sensor 140 in FIG. 16 and for sensor 240 in FIG. 17.

After the selected test sequence is complete, controller 36 performs the range of motion calculations, eliminating the effects of secondary motion, and calculates impairment. Then, for example, as seen in FIG. 19, the results can be printed. As an example, in testing cervical flexion, as shown in FIG. 18a, assuming that both the primary and secondary sensors 140 measure zero degrees with the person being tested in the neutral position and further assuming that the primary sensor 140 measures 22 degrees and the secondary sensor 140 measures 2 degrees with the person being tested having his head tilted fully forward; the controller 36 would determine that the person had tilted his head forward 22 degrees, but, at the spinal location of the secondary sensor, had also tilted his spine forward 2 degrees. Therefore, the primary 22 degree reading would be adjusted by the secondary 2 degree reading to determine that the measured cervical flexion was 20 degrees. If this is the "best" measurement of cervical flexion for the at least three tests of the person being tested, this 20 degree result will be shown on the printout of FIG. 19.

The apparatus 10 of FIG. 1 has no means for long term storage of data. Therefore, once a test sequence is completed and before conducting another test sequence, the results must be printed. With proper interface, instead of connecting printer 200 to main console 20 by plugging cable 202 into jack 54, a cable can connect a "smart" device which can receive the printout data and store or further manipulate the data. For example, historic files by patient identification can be maintained which permit automated comparisons of test data over time. Another alternative, as seen in FIGS. 20a-b, is to provide a PC interface card 222 which plugs into a personal computer 220 and interfaces the primary and secondary sensors (140 or 240) to the computer 220. Computer 220 can then be similarly programmed, as shown in FIGS. 14-17, like the "LITTLE GIANT" controller 36 of the previously described preferred embodiments. Computer 220 can be used for standard PC functions in addition to being used to perform range of motion/impairment testing. Computer 220 can also easily provide data storage means, for example on a hard or floppy disk, and can easily permit data manipulation not permitted by the "LITTLE GIANT" controller 36.

The foregoing detailed description is given primarily for clearness of understanding and no unnecessary limitations are to be understood therefrom for modifications can be made by those skilled in the art upon reading this disclosure and may be made without departing from the spirit of the invention and scope the appended claims.

What is claimed is:

1. A human body angle measuring apparatus, comprising:
   a. a support, said support having a preselected zero degree point;
   b. a shaft, said shaft rotatably connected to said support and protruding perpendicularly therefrom;
   c. a ring magnet connected to said shaft, said ring magnet having an outer cylindrical surface, said ring magnet being parallel to said support;
   d. a first Hall effect transducer, said first transducer connected to said support at a first preselected location and protruding perpendicularly therefrom, said first transducer being proximate said outer cylindrical surface of said ring magnet, said first transducer providing a first voltage output signal, said first voltage output signal representing a measurable first transducer magnetic field intensity;
   e. a second Hall effect transducer, said second transducer connected to said support at a second preselected location and protruding perpendicularly therefrom, said second transducer being proximate said outer cylindrical surface of said ring magnet, said second transducer providing a second voltage output signal, said second voltage output signal representing a measurable second transducer magnetic field intensity;
   f. means for evaluating said first voltage output signal and said second voltage output signal to determine an inclination angle, said inclination angle representing a measure of tilt of said support from said preselected zero degree point.

2. The apparatus of claim 1, wherein said first preselected location lies on a first line from said shaft to said first transducer and said second preselected location lies on a second line from said shaft to said second transducer, said first line and said second line having an arc of 120 degrees therebetween.

3. A human body range of motion determining apparatus, comprising:
   a. a primary sensor, said primary sensor producing at least one primary output signal, said at least one primary output signal representing an angle of inclination of said primary sensor;
   b. a secondary sensor, said secondary sensor producing at least one secondary output signal, said at least one secondary output signal representing an angle of inclination of said secondary sensor; and,
   c. means for controlling said apparatus, said controlling means communicating with said primary sensor and said secondary sensor, said controlling means including means for initially evaluating said at least one primary output signal to determine a primary calibration angle of inclination and initially evaluating said at least one secondary output signal to determine a secondary calibration angle of inclination, means for evaluating said at least one primary output signal to determine a primary angle of inclination and evaluating said at least one secondary output signal to determine a secondary angle of inclination, means for comparing said primary angle of inclination and said primary calibration angle of inclination to determine a primary range of motion, means for comparing said secondary angle of inclination and said secondary calibration angle of inclination to determine a secondary range of motion, and means for comparing said primary range of motion and said secondary range of motion to determine an actual range of motion.

4. The apparatus of claim 3, wherein said primary sensor is pivotally attached to a helmet assembly to be worn by a person undergoing range of motion testing, said primary sensor being alignable to be oriented in a desired vertical plane.

5. The apparatus of claim 3, wherein said at least one primary output signal comprises a first signal and a second signal and wherein said primary sensor includes:
   a. a support, said support having a preselected zero degree point;
   b. a shaft, said shaft rotatably connected to said support and protruding perpendicularly therefrom;
   c. a ring magnet connected to said shaft, said ring magnet having an outer cylindrical surface, said ring magnet being parallel to said support;
   d. a first Hall effect transducer, said first transducer connected to said support at a first preselected location and protruding perpendicularly therefrom, said first transducer being proximate said outer cylindrical surface of said ring magnet, said first transducer providing said first signal; and,
   e. a second Hall effect transducer, said second transducer connected to said support at a second preselected location and protruding perpendicularly therefrom, said second transducer being proximate said outer cylindrical surface of said ring magnet, said second transducer providing said second signal.

6. The apparatus of claim 3, wherein said at least one secondary output signal comprises a first signal and a second signal and wherein said secondary sensor includes:
   a. a support, said support having a preselected zero degree point;
   b. a shaft, said shaft rotatably connected to said support and protruding perpendicularly therefrom;
   c. a ring magnet connected to said shaft, said ring magnet having an outer cylindrical surface, said ring magnet being parallel to said support;
   d. a first Hall effect transducer, said first transducer connected to said support at a first preselected location and protruding perpendicularly therefrom, said first transducer being proximate said outer cylindrical surface of said ring magnet, said first transducer providing said first signal; and,
   e. a second Hall effect transducer, said second transducer connected to said support at a second preselected location and protruding perpendicularly therefrom, said second transducer being proximate said outer cylindrical surface of said ring magnet, said second transducer providing said second signal.

7. The apparatus of claim 3, wherein said at least one primary output signal comprises a first, second, third, fourth, fifth, and sixth signal and wherein said primary sensor is a capacitive sensor, said capacitive sensor having a first plate and a second plate, said first and said second plates being in a parallel relationship, said first and said second plates being contained by a grounded case, said first and said second plates having a space therebetween, said space therebetween being partway filled with a conducting fluid; said first plate having adjacent first, second, and third conductive sectors; said second plate having adjacent fourth, fifth, and sixth conductive sectors; said first, second, and third conductive sectors having a sixty degree off-set from said fourth, fifth, and sixth conductive sectors; said first conductive sector providing said first signal, said second conductive sector providing said second signal, said third conductive sector providing said third signal, said fourth conductive sector providing said fourth signal, said fifth conductive sector providing said fifth signal, and said sixth conductive sector providing said sixth signal.

8. The apparatus of claim 3, wherein said at least one secondary output signal comprises a first, second, third, fourth, fifth, and sixth signal and wherein said secondary sensor is a capacitive sensor, said capacitive sensor having a first plate and a second plate, said first and said second plates being in a parallel relationship, said first and said second plates being contained by a grounded case, said first and said second plates having a space therebetween, said space therebetween being partway filled with a conducting fluid; said first plate having adjacent first, second, and third conductive sectors; said second plate having adjacent fourth, fifth, and sixth conductive sectors; said first, second, and third conductive sectors having a sixty degree off-set from said fourth, fifth, and sixth conductive sectors; said first conductive sector providing said first signal, said second conductive sector providing said second signal, said third conductive sector providing said third signal, said fourth conductive sector providing said fourth signal, said fifth conductive sector providing said fifth signal, and said sixth conductive sector providing said sixth signal.

9. The apparatus of claim 3, wherein said controlling means further includes means for conducting additional range of motion testing to determine at least one additional actual range of motion and means for comparing said actual range of motion and said at least one additional actual range of motion to determine if said actual range of motion and said at least one additional actual range of motion are within a preselected range of motion tolerance.

10. The apparatus of claim 9, wherein said controlling means further includes means for indicating to a person undergoing range of motion testing when said primary sensor is positioned at said primary calibration angle of inclination and when said secondary sensor is positioned at said secondary calibration angle of inclination.

11. The apparatus of claim 3, wherein said at least one primary output signal comprises at least two signals and wherein said controlling means further includes means for evaluating said at least two signals to determine linearity.

12. The apparatus of claim 3, wherein said at least one secondary output signal comprises at least two signals and wherein said controlling means further includes means for evaluating said at least two signals to determine linearity.

13. The apparatus of claim 3, wherein said controlling means further includes means for calculating impairment using said determined actual range of motion.

14. The apparatus of claim 3, wherein said controlling means further includes means for selecting from a plurality of possible range of motion tests.

15. The apparatus of claim 14, wherein said plurality of possible range of motion tests include tests of a person's cervix, a person's thorax, a person's lumbar, and a person's extremities.

16. A method of determining range of motion comprising the steps of:
   a. placing a helmet having a primary sensor on a head of a person to be tested;
   b. positioning said person to be tested in a neutral test position;
   c. selecting a range of motion test to be conducted;
   d. aligning said primary sensor for said selected test;
   e. aligning a secondary sensor in a desired body location of said person to be tested;
   f. calibrating a range of motion apparatus which is in communication with said primary and said secondary sensors;
   g. having said person to be tested move from said neutral test position to a range of motion measurement position; and,
   h. activating said range of motion apparatus to determine an actual range of motion.

17. The method of claim 16, further including the steps of:
   a. returning said person to be tested to said neutral position;
   b. having said person to be tested again move from said neutral test position to a range of motion measurement position;
   c. activating said range of motion apparatus again to determine an additional actual range of motion; and
   d. reaccomplishing said range of motion test if said range of motion apparatus indicates an invalid test because said actual range of motion and said additional actual range of motion are not within a preselected range of motion tolerance.

* * * * *